(12) United States Patent
Luebke et al.

(10) Patent No.: US 8,907,105 B1
(45) Date of Patent: Dec. 9, 2014

(54) 1,2,3-TRIAZOLIUM IONIC LIQUIDS

(75) Inventors: David Luebke, Bethel Park, PA (US);
Hunaid Nulwala, Upper Saint Clair, PA
(US); Chau Tang, Green Brook, NJ (US)

(73) Assignee: U.S. Department of Energy,
Washington, DC (US)

( * ) Notice: Subject to any disclaimer, the term of this patent is extended or adjusted under 35 U.S.C. 154(b) by 174 days.

(21) Appl. No.: 13/223,465

(22) Filed: Sep. 1, 2011

(51) Int. Cl.
*C07D 249/04* (2006.01)
*A61K 31/4192* (2006.01)

(52) U.S. Cl.
USPC ........................................ 548/255; 514/381

(58) Field of Classification Search
CPC .................................................... C07D 249/04
USPC ............................................. 548/255, 262.2
See application file for complete search history.

(56) References Cited

U.S. PATENT DOCUMENTS

| 7,645,883 | B1 * | 1/2010 | Hawkins et al. | 548/255 |
| 7,829,725 | B2 * | 11/2010 | Harmer et al. | 548/262.2 |
| 2009/0286976 | A1 * | 11/2009 | Lee et al. | 544/158 |

OTHER PUBLICATIONS

Zhou, et al. (JACS, 2005, vol. 127, pp. 10824-10825).*
Toppet, et al. (Organic Magnetic Resonance, vol. 11, No. 11, 1978, pp. 578-579.*
Toppet, et al. (Journal of Polymer Science: Polymer Letters Edition, 1976, vol. 14, pp. 389-394).*
Davies, et al. (J. Chem. Soc., (C), 1971, pp. 2572-2576.*
Fletcher et al, CA Plus Doc. 154:46016, 2010.*

* cited by examiner

*Primary Examiner* — Rebecca Anderson
*Assistant Examiner* — Karen Cheng
(74) *Attorney, Agent, or Firm* — John D. Cravero; Brian J. Lally; John T. Lucas

(57) ABSTRACT

The present invention relates to compositions of matter that are ionic liquids, the compositions comprising substituted 1,2,3-triazolium cations combined with any anion. Compositions of the invention should be useful in the separation of gases and, perhaps, as catalysts for many reactions.

5 Claims, 4 Drawing Sheets

1,2,3-TRIAZOLIUM IONIC LIQUIDS

GOVERNMENT INTEREST

The United States Government has rights in this invention pursuant to the employer-employee relationship between the Government and one or more of the inventors who are U.S. Department of Energy employees at the National Energy Technology Laboratory, Pittsburgh, Pa.

FIELD OF THE INVENTION

One or more embodiments consistent with the present disclosure relate to tri-substituted 1,2,3-triazolium ionic liquids, methods of their preparation and methods for using the compounds described in various applications, including but not limited to the purification or separation of gases.

BACKGROUND

Ionic liquids (IL) are organic salts that are commonly liquid at room temperature. ILs have also been defined as molten salts having a melting point below 100° C. Recent interest in room temperature ionic liquids has increased due to unique characteristics of those compounds, such as a unique solubility, negligible vapor pressure, a wide electrochemical window and good thermal stability. Due to the negligible vapor pressure of ILs, they have been identified as environmentally friendly as they would not contribute to air pollution or to the generation of potentially toxic emissions when used as a solvent. As a result of these advantageous characteristics, ILs have potential use in a number of applications, including but not limited to synthesis, as both solvents and catalysts; energy storage, as electrolytes; extraction of radioactive materials, metals and organic liquids; polymer processing; cellulose processing; and gas separations. However, due to the vast amount of structural configurations possible for an ionic liquid, estimated at up to $10^{18}$ available compounds, selection of appropriate compounds for the various applications can be intimidating.

ILs include triazolium salts, which consist of two isomeric compounds having aromatic 5-membered rings with three nitrogen and two carbon atoms on the ring as the cation. The two isomers are typically referred to as 1,2,4- or 1,2,3-triazolium salt based on the position of the nitrogen atoms, e.g., 1,2,3- refers to a salt where the three nitrogen atoms are adjacent to one another on the ring. Heterocyclic compounds based on 1,2,3-triazoles have been widely used due to their high biological activity, in antiviral, antimicrobial, antifungal medicines and agricultural chemicals. The 1,2,3-triazole heterocycle is commonly synthesized via Cu(I)-catalyzed 1,3-dipolar cycloaddition and Ru-cat of azides and alkynes, resulting in a 1,4-di-substituted 1,2,3-triazole core and 1,5-di-substituted 1,2,3-triazole core, respectively. However, synthesis and use of tri-substituted 1,2,3-triazolium salts in various applications has not been thoroughly explored.

For example, certain five and six-membered aromatic heterocyclic ILs have been identified as potential candidates in gas separation processes, particularly in U.S. Pat. No. 6,579,343, issued to Brennecke, et al. However, relative to the vast number of potential ILs, very few ILs have found widespread use for most applications, and gas separations in particular.

SUMMARY

One or more embodiments consistent with the present disclosure generally relate to a novel class of 1,2,3-triazolium-based cation species and ionic compounds that contain these cation species. These ionic compounds have improved properties over other classes of ionic compounds, including but not limited to increased CO solubility and polymerization capability in one or more embodiments.

The use of the 1,2,3-triazolium core to investigate the effect of structural changes on functional properties is advantageous due to the high modularity and regio-specificity of triazolium over other core compounds, such as ammonium, pyridinium, pyrrolidinium and imidazolium cores. Moreover, the click chemistry presented herein is an ideal platform to systematically probe properties of ILs due to excellent molecular control, ease of synthesis, benign reaction conditions and fidelity, in addition to the chemistry being modular, wide in scope, high yielding, stereospecific and insensitive to oxygen and water. In addition, the configuration of the multiple embodiments described herein create a greater dipole moment, which leads to greater thermal stability of the IL.

In one aspect, a tri-substituted-1,2,3-triazolium salt comprises a structure represented by formula (I):

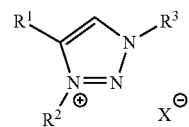

where $R^1$, $R^2$ and $R^3$ each are independently selected from the group consisting of:
  (i) H;
  (ii) halogen;
  (iii) $C_1$ to $C_{25}$ straight-chain, branched or cyclic alkane or alkene, optionally substituted with at least one member selected from the group consisting of Cl, Br, F, I, OH, $NH_2$ and SH;
  (iv) $C_1$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
  (v) $C_6$ to $C_{20}$ unsubstituted aryl, or $C_3$ to $C_{25}$ unsubstituted heteroaryl having one to three heteroatoms independently selected from the group consisting of O, N, Si and S; and,
  (vi) $C_6$ to $C_{25}$ substituted aryl, or $C_3$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:
    (1) $C_1$ to $C_{25}$ straight-chain, branched or cyclic alkane or alkene, optionally substituted with at least one member selected from the group consisting of Cl, Br, F I, OH, NH2 and SH,
    (2) OH,
    (3) $NH_2$, and,
    (4) SH;
  and where $X^-$ is an anion.

In some embodiments, the anion component, $X^-$, may comprise any suitable anionic species. By way of example, such anion species include any non-Lewis acid anion. Further by way of example, the anion component of the ionic triazolium-based compounds may comprise $PF_6$, $BF_4$, $NO_3$, halides, bromide (Br), iodide (I), bis(trifluoromethylsulfonyl)imide, ($N(SO_2CF_3)_2$ or $Tf_2N$), bis(methanesulfonyl)imide ($N(SO_2CH_3)_2$), dictanimide (dca, $N(CN)_2$), alkylsulfate, alkylsulfonates, saccharinate, triflate ($SO_3CF_3$), tosylate, acetate, lactate, tris(perfluoroalkyl)trifluorophosphate, trifluoroacetate, gluconate, ethylsulfate ($EtSO_4$), tetrafluoroborate ($BF_4$), docusate (doc), 2-(2-methoxy-ethoxy)-ethysulfate ($C_5H_{11}O_2SO_4$), methylsulfate ($MeSO_4$), acetate ($CH_3CO_2$), trifluoroacetate ($CF_3CO_2$), a mono- or diperfluorosulfonate, or any one of $(CF_3)_2PF_4$, $(CF_3)_3PF_3$, $(CF_3)_4PF_2$, $(CF_3)_5PF$, $(CF_3)_6P$, $SF_5CF_2SO_3$, $SF_5CHFCF_2SO_3$, $CF_3CF_2(CF_3)_2CO$, $(CF_3SO_2)_2CH$, $(SF_5)_3C$ or $(O(CF_3)_2C_2(CF_3)_2O)_2PO$, and amino acids including but not limited to glycine, histidine, glutamine, serine and leucine.

In one embodiment, the composition comprises 1-(2-(2-(2-methoxyethoxy)ethoxy)ethyl-3-methyl-4-vinyl-1H-1,2,3-triazol-3-ium bis[(trifluoromethyl)sulfonyl]amide, 1-(2-(2-(2-methoxyethoxy)ethoxy)ethyl-3-methyl-4-vinyl-1H-1,2,3-triazol-3-ium iodide, 3-methyl-1-(pyridine-4-yl)-4-vinyl-1H-1,2,3-triazol-3-ium iodide, 3-methyl-1-(pyridine-4-yl)-4-vinyl-1H-1,2,3-triazol-3-ium bis[(trifluoromethyl) sulfonyl]amide, 3-methyl-1-phenyl-4-vinyl-1H-1,2,3-triazol-3-ium iodide, 3-methyl-1-phenyl-4-vinyl-1H-1,2,3-triazol-3-ium bis[(trifluoromethyl)sulfonyl]amide, 1-benzyl-3-methyl-4-phenyl-1H-1,2,3-triazol-3-ium iodide, 1-benzyl-3-methyl-4-phenyl-1H-1,2,3-triazol-3-ium bis [(trifluoromethyl)sulfonyl]amide, 1-benzyl-3-methyl-4-propyl-1H-1,2,3-triazol-3-ium iodide, 1-benzyl-3-methyl-4-propyl-1H-1,2,3-triazol-3-ium bis[(trifluoromethyl) sulfonyl]amide, 1-hexyl-3-methyl-4-phenyl-1H-1,2,3-triazol-3-ium iodide, 1-hexyl-3-methyl-4-phenyl-1H-1,2,3-triazol-3-ium bis[(trifluoromethyl)sulfonyl]amide, 4-hexyl-3-methyl-1-phenyl-1H-1,2,3-triazol-3-ium iodide, 4-hexyl-3-methyl-1-phenyl-1H-1,2,3-triazol-3-ium bis [(trifluoromethyl)sulfonyl]amide, 1-hexyl-3-methyl-4-propyl-1H-1,2,3-triazol-3-ium iodide, 1-hexyl-3-methyl-4-propyl-1H-1,2,3-triazol-3-ium bis[(trifluoromethyl) sulfonyl]amide, 4-hexyl-3-methyl-1-propyl-1H-1,2,3-triazol-3-ium iodide, 4-hexyl-3-methyl-1-propyl-1H-1,2,3-triazol-3-ium bis[(trifluoromethyl)sulfonyl]amide, 1-{2-[2-(2-methoxyethoxy)ethoxy]ethyl}-3-methyl-4-phenyl-1H-1,2,3-triazol-3-ium iodide, 1-{2-[2-(2-methoxyethoxy)ethoxy] ethyl}-3-methyl-4-phenyl-1H-1,2,3-triazol-3-ium bis [(trifluoromethyl)sulfonyl]amide, 1-{2-[2-(2-methoxyethoxy)ethoxy]ethyl}-3-methyl-4-propyl-1H-1,2,3-triazol-3-ium iodide, 1-{2-[2-(2-methoxyethoxy)ethoxy] ethyl}-3-methyl-4-propyl-1H-1,2,3-triazol-3-ium bis [(trifluoromethyl)sulfonyl]amide, 3-methyl-4-phenyl-1-(pyridin-4-yl)-1H-1,2,3-triazol-3-ium iodide, 3-methyl-4-phenyl-1-(pyridin-4-yl)-1H-1,2,3-triazol-3-ium bis [(trifluoromethyl)sulfonyl]amide, 3-methyl-4-propyl-1-(pyridin-4-yl)-1H-1,2,3-triazol-3-ium iodide, 3-methyl-4-propyl-1-(pyridin-4-yl)-1H-1,2,3-triazol-3-ium bis [(trifluoromethyl)sulfonyl]amide, 3-methyl-4-phenyl-1-((trimethylsilyl)methyl)-1H-1,2,3-triazol-3-ium iodide, 3-methyl-4-phenyl-1-((trimethylsilyl)methyl)-1H-1,2,3-triazol-3-ium bis[(trifluoromethyl)sulfonyl]amide, 3-methyl-1-phenyl-4-((trimethylsilyl)methyl)-1H-1,2,3-triazol-3-ium iodide, 3-methyl-1-phenyl-4-((trimethylsilyl)methyl)-1H-1,2,3-triazol-3-ium bis[(trifluoromethyl)sulfonyl]amide, 3-methyl-4-propyl-1-((trimethylsilyl)methyl)-1H-1,2,3-triazol-3-ium iodide, 3-methyl-4-propyl-1-((trimethylsilyl)methyl)-1H-1,2,3-triazol-3-ium bis[(trifluoromethyl)sulfonyl] amide, 3-methyl-1-propyl-4-((trimethylsilyl)methyl)-1H-1,2,3-triazol-3-ium iodide, and 3-methyl-1-propyl-4-((trimethylsilyl)methyl)-1H-1,2,3-triazol-3-ium bis [(trifluoromethyl)sulfonyl]amide.

Also provided is a method of separating a gas from a gaseous mixture comprising the steps of contacting the gaseous mixture with an ionic liquid, wherein said ionic liquid has a composition as described above. In an additional embodiment of the method, the ionic liquid is provided as a supported ionic liquid membrane. In yet another embodiment, the ionic liquid is used to separate carbon dioxide from a gaseous stream.

As described herein, an ionic liquid selectively solubilizes select impurities, leaving a desired gas in a gas stream. In an exemplary embodiment, a gas stream containing impurities such as carbon dioxide may be processed using ionic liquids of the present invention to provide a purified gas stream. It is appreciated that the gas stream containing impurities may be contact with the ionic liquid by conventional methods known to one of ordinary skill in the art.

BRIEF DESCRIPTION OF THE DRAWINGS

These and other features, aspects, and advantages of the multiple embodiments of the present invention will become better understood with reference to the following description, appended claims, and accompanied drawings where:

Figure 1:
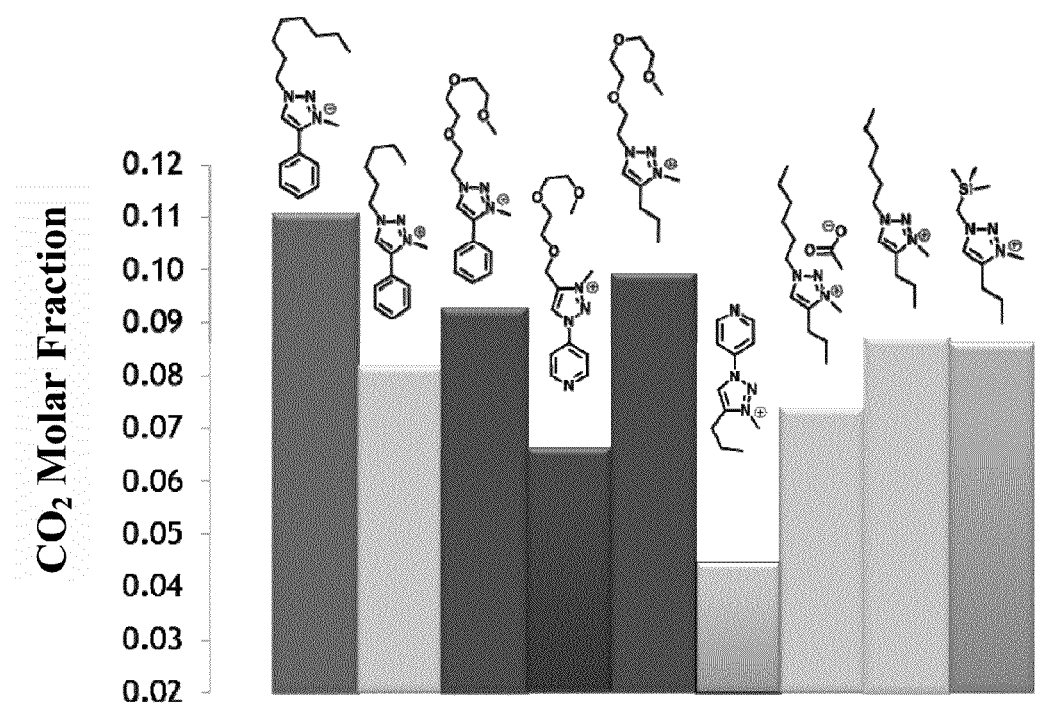
FIG. 1 is a graphical representation of $CO_2$ solubility (molar fraction) of various embodiments with a $Tf_2N$ anion at 37° C. and 3 bar.
Figure 2:
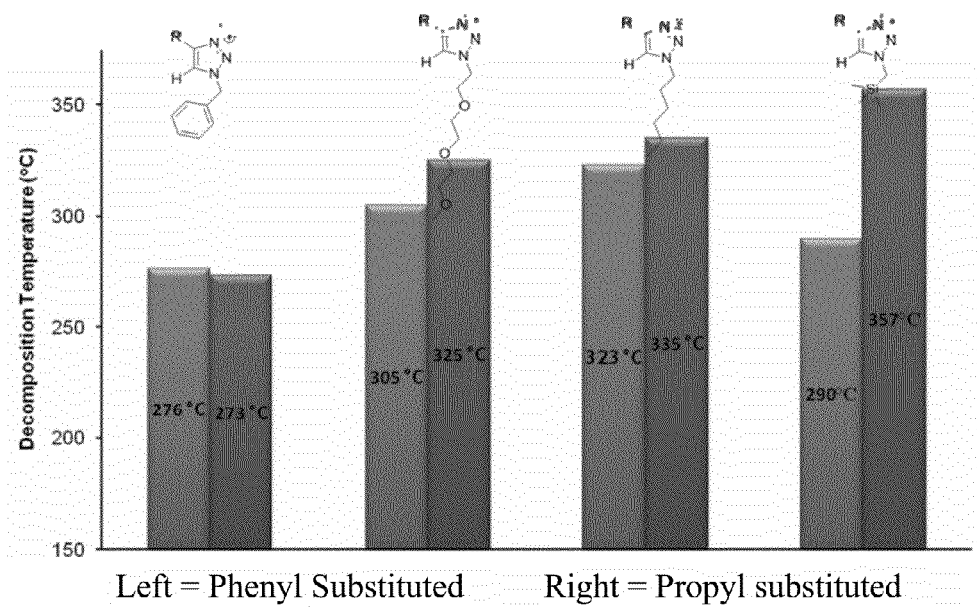
FIG. 2 is a graphical representation of the thermal decomposition temperature of various embodiments with $Tf_2N$ as the anion.

The details of some exemplary embodiments of the methods and systems of the present disclosure are set forth in the description below. Other features, objects, and advantages of the disclosure will be apparent to one of skill in the art upon examination of the following description, drawings, examples and embodiments. It is intended that all such additional systems, methods, features, and advantages be included within this description, be within the scope of the present disclosure.

DETAILED DESCRIPTION

Ionic liquids of one or more embodiments of the present invention relate to quaternary five-membered-ring heterocycles having three adjacent nitrogen atoms such as tri-substituted, 1,2,3,-triazolium salts.

One or more embodiments of the present inventions relate to the use of ionic liquids to separate an impurity from a gas stream. The gas stream may be contacted with one or more ionic liquids to separate a component gas from the gas stream due to the preferential solubility and/or diffusibility of the component gas in the ionic liquid. An illustrative embodiment is a method to purify industrial effluent stream by removing impurities, such as carbon dioxide, by contacting the effluent stream with an ionic liquid as described herein.

For purposes of this disclosure, it is understood that gas and gas streams may refer to vapors (volatilized liquids), gaseous compounds, and/or gaseous elements.

Contacting the ionic liquid with the gas stream may be accomplished in a variety of ways and should be optimized to increase mixing and contact between the ionic liquid and gas stream for a sufficient time to allow significant removal of the target gas. More specifically, systems having high surface contact areas are desirable. As one example, the ionic liquid may be contained within a supported liquid membrane or use of conventional absorbers, such as counter current and similar absorbers.

Supported liquid membranes comprise a solvent such as an ionic liquid contained within the pores of a solid microporous support such as ceramic, metal or polymer support. Ionic liquids contained in such support may be used at temperatures greater than ambient temperature to achieve more rapid separation, requiring less contact time. Microporous supports suitable for use with the present invention are well known in the art, including but not limited to U.S. Pat. Nos. 3,426,754; 3,801,404; 3,839,516; 3,843,761; 3,843,762; 3,920,785; 4,055,696; 4,255,376; 4,257,997; 4,359,510; 4,405,688 and 4,438,185, which are incorporated by reference herein. The supported liquid membranes may be fabricated as thin films or hollow fibers with continuous networks of interconnected pores leading from one surface to the other. Supported liquid membranes contact a feed gas mixture on one side of the membrane and may affect separation of a target gas component from the mixture by allowing that component to escape via permeation or diffusion into the ionic liquid and through the liquid membrane.

In additional embodiments, the ionic liquid may be contacted with the gaseous mixture in conventional, fixed bed gas/liquid absorption systems or a flow apparatus. In a fixed bed absorption system, the ionic liquid may be coated on a solid support to increase surface area of the ionic liquid capable of solubilizing the target gas. The above systems may be operated is co-current or counter-current dual flow mode to achieve the desired level of mixing, with subsequent regeneration of the ionic liquid prior to introduction to the purification unit.

DEFINITIONS

In describing the disclosed subject matter, the following terminology will be used in accordance with the definitions set forth below.

The term "heteroaryl" refers to an aryl group having one or more heteroatoms.

When referring to an alkane or alkene, the term "optionally substituted with at least one member selected from the group consisting of" means that one or more hydrogens on the carbon chain may be independently substituted with one or more of at least one member of the group. For example, substituted $C_2H_5$ may be, without limitations, $CF_2CF_3$, $CH_2CH_2OH$ or $CF_2CF_2I$.

The expression "$C_1$ to $C_n$ straight-chain, branched," where n is an integer defining the length of the carbon chain, is meant to indicate that $C_1$ and $C_2$ are straight-chain, and $C_3$ to $C_n$ may be straight-chain or branched.

The term "alkoxy" refers to a straight-chain or branched alkyl group bound via an oxygen atom and includes but is not limited to an alkoxy group bound to an alkane, alkene or aryl group, such as an ether group.

In one embodiment, the five-membered-ring heterocycle having three adjacent nitrogen atoms comprises a compound having the structure of Formula I:

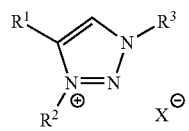

Formula I where $R^1$, $R^2$ and $R^3$ each are independently selected from the group consisting of:
(i) H;
(ii) halogen;
(iii) $C_1$ to $C_{25}$ straight-chain, branched or cyclic alkane or alkene, optionally substituted with at least one member selected from the group consisting of Cl, Br, F, I, OH, $NH_2$ and SH;
(iv) $C_1$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
(v) $C_6$ to $C_{20}$ unsubstituted aryl, or $C_3$ to $C_{25}$ unsubstituted heteroaryl having one to three heteroatoms independently selected from the group consisting of O, N, Si and S; and,
(vi) $C_6$ to $C_{25}$ substituted aryl, or $C_3$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:
(1) $C_1$ to $C_{25}$ straight-chain, branched or cyclic alkane or alkene, optionally substituted with at least one member selected from the group consisting of Cl, Br, F I, OH, $NH_2$ and SH,
(2) OH,
(3) $NH_2$, and,
(4) SH;
and wherein $X^-$ is an anion.

The term "anion" refers to an ion having a negative charge. Preferably, anions include but are not limited to hydroxide, chloride, bromide, iodide, borate, tetrafluoroborate, cuprate, $Cu(I)Cl_2$ anion, phosphate, hexafluorophosphate, hexafluoroantimonate, perchlorate, bis[(trifluoromethyl)sulfonyl] amide, nitrite, nitrate, sulfate, a carboxylate, a sulfonate, a sulfonamide, a phosphonate, $PF_6$, $BF_4$, $NO_3$, halides, bis(trifluoromethylsulfonyl)imide, ($N(SO_2CF_3)_2$ or $Tf_2N$), bis(methanesulfonyl)imide ($N(SO_2CH_3)_2$), dictanimide (dca, $N(CN)_2$), alkylsulfate, alkylsulfonates, saccharinate, triflate ($SO_3CF_3$), tosylate, acetate, lactate, tris(perfluoroalkyl)trifluorophosphate, trifluoroacetate, gluconate, ethylsulfate ($EtSO_4$), tetrafluoroborate ($BF_4$), docusate (doc), 2-(2-methoxy-ethoxy)-ethysulfate ($C_5H_{11}O_2SO_4$), methylsulfate ($MeSO_4$), acetate ($CH_3CO_2$), trifluoroacetate ($CF_3CO_2$), a mono- or dipernuorosulfonate. or any one of $(CF_3)_2PF_4$, $(CF_3)_3PF_3$, $(CF_3)_4PF_2$, $(CF_3)_5PF$, $(CF_3)_6P$, $SF_5CF_2SO_3$, $SF_5CHFCF_2SO_3$, $CF_3CF_2(CF_3)_2CO$, $(CF_3SO_2)_2CH$, $(SF_5)_3C$ and $(O(CF_3)_2C_2(CF_3)_2O)_2PO$ and amino acids including but not limited lo glycine, .histidine, glutaminc, serine and leucine.

In additional embodiments, $R^1$, $R^2$ and $R^3$ are each independently selected from the group consisting of:
(i) halogen;
(ii) $C_1$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, NH$_2$ and SH;
(iii) C$_3$ to C$_{25}$ unsubstituted heteroaryl having one to three heteroatoms independently selected from the group consisting of O, N, Si and S;
(iv) C$_6$ to C$_{25}$ substituted aryl, or C$_3$ to C$_{25}$ substituted heteroaryl having one to three heteroatoms independently selected from the group consisting of O, N, Si and S; and wherein said substituted aryl or substituted heteroaryl has one to three substituents independently selected from the group consisting of:
(1) C$_1$ to C$_{25}$ straight-chain, branched or cyclic alkane or alkene, optionally substituted with at least one member selected from the group consisting of Cl, Br, F I, OH, NH$_2$ and SH,
(2) OH,
(3) NH$_2$, and,
(4) SH;
and wherein X$^-$ is an anion.

In one or more specific embodiments, R$^1$ or R$^3$ is a C$_2$ to C$_5$ alkene. Even more specifically, in one or more embodiments, R$^1$ or R$^3$ is a vinyl group.

In yet another embodiment, R$^1$ is a vinyl group.

In yet another embodiment, R$^3$ is a C$_2$ to C$_{10}$ straight chain alkane comprising one to three oxygen atoms. Even more preferably, R$^3$ is a C$_7$ straight chain alkane having three oxygen atoms.

In yet another embodiment, R$^1$ is a vinyl group, R$^3$ is an alkoxy group, R$^2$ is a C$_1$ to C$_{10}$ alkane and X$^-$ is selected from the group consisting of iodide, bromide, chloride, acetate and Tf$_2$N.

In another embodiment, R$^3$ is a C$_2$ to C$_5$ alkene and even more preferably R$^3$ is a vinyl group.

In yet another embodiment, R$^3$ is a C$_2$ to C$_5$ alkene and R$^1$ is an unsubstituted aryl, and even more preferably R$^3$ is a vinyl group and R$^1$ is a phenyl group.

In yet another embodiment, R$^1$ is a protected amino group.

In yet another embodiment, R$^1$ is a C$_1$ to C$_{25}$ straight-chain, branched or cyclic alkane substituted with at least one —NH$_2$ group and R$^3$ is C$_2$ to C$_{10}$ straight chain alkane comprising one to three oxygen atoms. Even more preferably, R$^3$ is a C$_7$ straight chain-alkane having three oxygen atoms.

In yet another embodiment, R$^3$ is a C$_6$ to C$_{25}$ substituted heteroaryl having one to three nitrogen atoms. Even more preferably, R$^3$ is a C$_5$ substituted heteroaryl having 1 nitrogen atom, also known as pyridine.

In yet another embodiment, R$^3$ is a C$_6$ to C$_{25}$ substituted heteroaryl having one to three nitrogen atoms and R$^1$ is a C$_6$ to C$_{25}$ unsubstituted aryl group. Even more preferably, R$^3$ is a pyridine and R$^1$ is a phenyl group.

In yet another embodiment, R$^1$ is a C$_1$ to C$_{25}$ straight-chain or branched alkane comprising one to three silicon atoms. Even more preferably, R$^1$ is a silyl group having three methyl groups, commonly referred to as a trimethylsilyl group.

In yet another embodiment, R$^1$ is a C$_1$ to C$_{25}$ straight-chain or branched alkane comprising one to three silicon atoms and R$^3$ is either a C$_1$ to C$_{12}$ straight-chain or branched alkane or a C$_5$ to C$_{10}$ unsubstituted aryl group. Even more preferably, R$^1$ is a silyl and R$^3$ is a phenyl or alkyl group.

In yet another embodiment, R$^3$ is a C$_1$ to C$_{25}$ straight-chain or branched alkane comprising one to three silicon atoms. Even more preferably, R$^3$ is a silyl group having three methyl groups.

In yet another embodiment, R$^3$ is a C$_1$ to C$_{25}$ straight-chain or branched alkane comprising one to three silicon atoms and R$^1$ is a C$_1$ to C$_{12}$ straight-chain or branched alkane or a C$_5$ to C$_{10}$ unsubstituted aryl group.

In another embodiment, R$^3$ is a C$_1$ to C$_{25}$ straight-chain, branched or cyclic alkane or alkene substituted with at least one fluorine atom.

In yet another embodiment, R$^3$ is a C$_1$ to C$_{25}$ straight-chain, branched or cyclic alkane or alkene substituted with at least one fluorine atom and R$^1$ is a C$_5$ to C$_{10}$ unsubstituted aryl group.

In another embodiment, R$^1$ is a C$_2$ to C$_{10}$ straight chain alkane comprising one to three oxygen atoms. Even more preferably R$^1$ is a C$_7$ straight-chain alkane comprising three oxygen atoms.

In yet another embodiment, R$^1$ is a C$_2$ to C$_{10}$ straight chain alkane comprising one to three oxygen atoms and R$^3$ is a C$_6$ to C$_{25}$ substituted heteroaryl having one to three nitrogen atoms. More preferably, R$^1$ is a C$_7$ straight chain alkoxy having three oxygen atoms and R$^3$ is a pyridine group.

The multiple embodiments will be further described with reference to the following Examples. However, the examples below are to be construed as merely illustrative, and not limiting of the remainder of the disclosure in any way whatsoever. Without further elaboration, it is believed that one skilled in the art can, based on the description herein, utilize the present disclosure to its fullest extent and perform the methods and systems disclosed herein. All publications recited herein are hereby incorporated by reference in their entirety.

General Synthesis of Tri-Substituted 1,2,3-Triazolium Ionic Liquids

The present example demonstrates general methods that may be used in the synthesis of the triazolium-based ionic compounds of the present invention. However, many other reagents and modification to the steps described below may also be used in accordance with the multiple embodiments of the present invention.

General Reaction to Form Triazolium-Based ILs

The general procedure for the preparation of 1,2,3-triazolium ILs follows the reaction outlined in Equation 1.

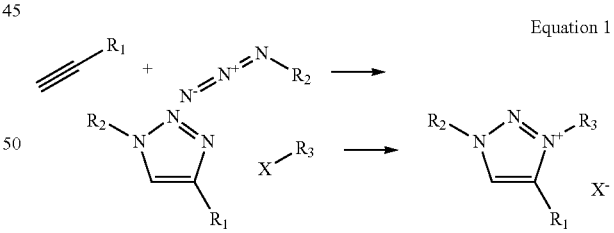

Equation 1

More specifically, alkyne, azide CuSO$_4$ and sodium ascorbate are added to an aqueous medium. The resulting triazole can subsequently be refluxed with excess X—R$^3$.

In another embodiment, ionic liquids of the present invention can be obtained through Cu-catalyzed click chemistry utilizing a heterogeneous catalyst, such as Cu/C according to Nulwala, H., et al., *Macromolecules*, 2009, 42, 6068 and Lipshutz, B. H. and Taft, B. R., *Angew. Chem.* 2006, 118, 8415, which are incorporated by reference herein.

The IL can further be modified by changing the anion through an ion exchange reaction as generally described by Equation 2, where M is a metal and Y is the desired anion.

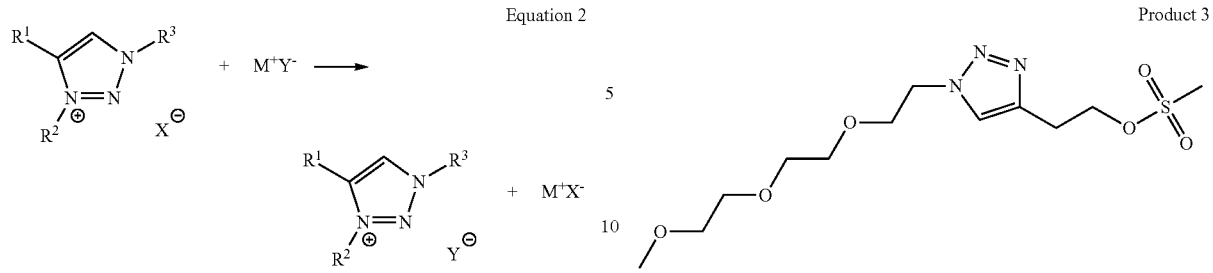

Equation 2

Tri-substituted 1,2,3-triazolium ionic liquids obtained as described above can further undergo ion exchange to obtain the desired anionic component. This desired compound can be obtained by mixing the ionic liquid with a metal salt possessing the desired anion and refluxing.

Example 1

Preparation of 1-(2-(2-(2-methoxyethoxy)ethoxy)ethyl-3-methyl-4-vinyl-1H-1,2,3-triazol-3-ium bis[(trifluoromethyl)sulfonyl]amide Formation of the alkyl azide (Product 1) was accomplished by placing 4.60 g of sodium azide in a 125 mL flask, followed by addition of 5.25 g of CMT 91 with a pipette.

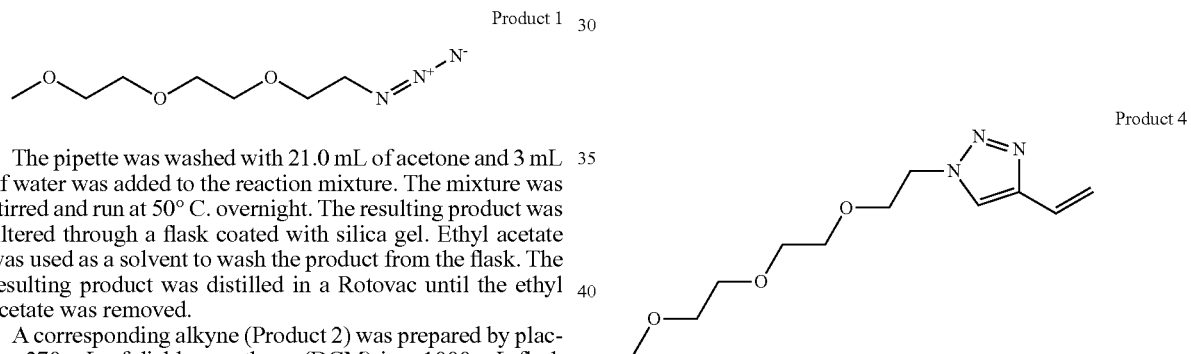

Product 1

The pipette was washed with 21.0 mL of acetone and 3 mL of water was added to the reaction mixture. The mixture was stirred and run at 50° C. overnight. The resulting product was filtered through a flask coated with silica gel. Ethyl acetate was used as a solvent to wash the product from the flask. The resulting product was distilled in a Rotovac until the ethyl acetate was removed.

A corresponding alkyne (Product 2) was prepared by placing 270 mL of dichloromethane (DCM) in a 1000 mL flask and adding 10.0 g of 3-butyn-1-ol.

Product 2

28.0 mL of triethylamine was added to the DCM solution, which was subsequently stirred and cooled on ice. In addition, 13.5 mL of mesyl chloride was added at a rate of one drop per second until complete and the solution was stirred and placed in an ice bath overnight. The reaction mixture was purified by washing twice with 100 mL of water in a 500 mL separatory funnel. The organic layer was washed with 100 mL of HCl, followed by a wash with 100 mL of sodium carbonate. The aqueous layers were discarded and the organic layer was dried over magnesium sulfate, which was later filtered off using vacuum filtration. Finally, the solution containing Product 2 was distilled.

The 1,2,3-triazole core (Product 3) was formed by adding Product 1 and Product 2 to a 250 mL flask and mixed with 100 mL of 2:1 (w/w) t-butanol to water mixture, which was then stirred.

Product 3

A copper sulfate crystal was dissolved in 10 mL of water and added to reaction mixture, followed by addition of a few grams of sodium ascorbate, which turned the mixture yellow. The reaction was stirred overnight and additional sodium ascorbate was added to ensure completion of the reaction. The solution containing Product 3 was purified by distilling the reaction mixture to the boiling point of water and passing the product through a filter flask coated in silica gel. The flask was washed with an ethyl acetate solvent, which was collected and distilled to remove ethyl acetate.

A vinyl group was attached to Product 3 to form Product 4 by adding 3.53 g of sodium iodide, 9.50 mL of triethylamine and 117 mL of dioxane to the flask with Product 3.

Product 4

The reaction mixture was stirred and refluxed at 119° C. The heat was turned off after an hour and the reaction mixture stirred overnight. TLC was run on the reaction mixture containing Product 4, producing three spots under ultraviolet light. The solution was distilled for 20 minutes. Afterwards, diethyl ether was added to Product 4 and ethyl acetate used to wash the flask to dissolve any solids. The remaining solution was filtered using a Buchner funnel and further distilled. Product 4 was loaded onto a silica gel plate and placed on top of 50 mL silica gel column. A column was run using a gradient solvent, starting with 75% hexanes and 25% ethyl acetate, stepping up to 100% ethyl acetate. The collected samples (50 mA threshold) were combined in a 1000 mL flask and distilled in a Rotovac.

To the pot containing Product 4 was added 2 mL of methyl iodide, which was stirred for two hours. 5 mL of acetonitrile and an additional 2 mL of methyl iodide were added and the reaction mixture was stirred and refluxed overnight at 40° C. to give Product 5.

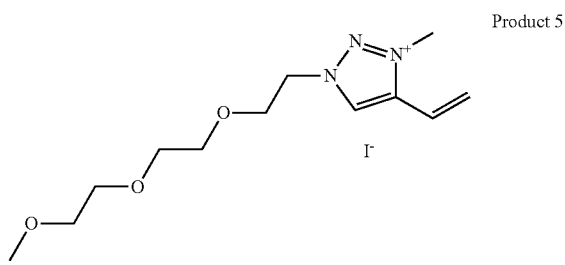 [SMILES: C=Cc1cn(CCOCCOCCOC)n[n+]1C ; [I-]]

Product 5

Ion exchange of Product 5 was performed by placing 10 mL of water in a flask containing Product 5 and adding 1.743 g of lithium bis[(trifluoromethyl)sulfonyl]amide. The reaction mixture was stirred and refluxed overnight at 80° C. to yield the salt of Product 6.

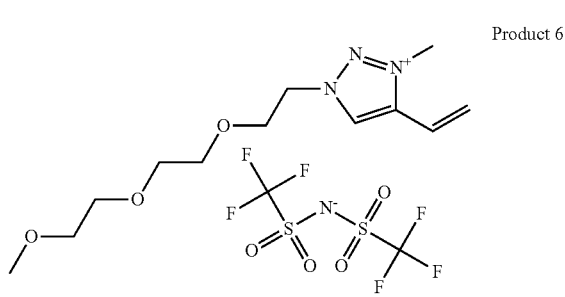 [SMILES: C=Cc1cn(CCOCCOCCOC)n[n+]1C ; O=S(=O)([N-]S(=O)(=O)C(F)(F)F)C(F)(F)F]

Product 6

Product 6 was purified by adding 20 mL of dichloromethane to the reaction mixture and washing four times with 20 mL of pure water. The aqueous layers were discarded and the organic layer was distilled in a Rotovac.

Example 2

Preparation of 3-methyl-1-(pyridine-4-yl)-4-vinyl-1H-1,2,3-triazol-3-ium iodide

In a vial containing dioxane, 2-(1-(pyridin-4-yl)-1H-1,2,3-triazol-4-yl)ethyl methanesulfonate (2 g, 7.45 mmol), sodium iodide (3.49 g, 23.26 mmol) and triethylamine (1.04 ml, 7.45 mmol) were added. The reaction was heated at 100° C. for 1 hour. The salt was filtered and rinse with more dioxane. The solvent was removed and the product was purified by biotage with 3 CV EA, 2 CV 9/1 EA/methanol ramp and 10 CV EA/methanol. After collecting all fraction and concentration of solvent, a solid product was obtained to give 0.75 g solid product of 4-(4-vinyl-1H-1,2,3-triazol-1-yl)pyridine.

4-(4-vinyl-1H-1,2,3-triazol-1-yl)pyridine (0.70 g, 4.07 mmol) and iodomethane (5 ml, 80 mmol) were added to a vial with acetonitrile. The reaction was heated for at 40° C. for 2 hours, the reaction was completed as confirmed by TLC. The precipitate was filtered and rinsed with ethyl acetate.

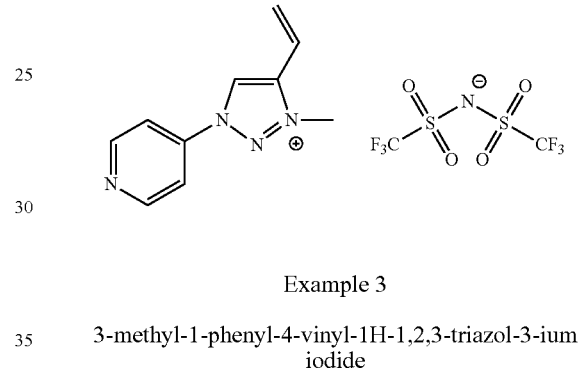

3-methyl-1-(pyridin-4-yl)-4-vinyl-1H-1,2,3-triazol-3-ium iodide (1.28 g, 4.07 mmol) and lithium bis((trifluoromethyl)sulfonyl)amide (1.31 g, 4.55 mmol) were added to a vial with methanol to which 4 mL of water was added to create a soluble mixture. The reaction was stirred at room temperature for 22 hours. The solvent was removed. Ethyl acetate was used to dissolve the product. The solution was washed three times with 10 mL water, dried with MgSO$_4$, filtered and concentrated. The product is a solid and the following structure was confirmed by NMR:

Example 3

3-methyl-1-phenyl-4-vinyl-1H-1,2,3-triazol-3-ium iodide 2-(1-phenyl-1H-1,2,3-triazol-4-yl)ethyl methanesulfonate (1.43 g, 5.35 mmol), triethylamine (1.62 g, 16.05 mmol) and sodium iodide (2.41 g, 16.05 mmol) were added to a vial to produce 1-phenyl-4-vinyl-1H-1,2,3-triazole.

1-phenyl-4-vinyl-1H-1,2,3-triazole (0.9 g, 5.26 mmol) and iodomethane (37.3 g, 263 mmol) were mixed and stirred overnight. Water was added and the salt was extracted in water. The water was removed under vacuum and the precipitate was washed with acetone and the acetone was decanted yielding pale yellow crystals.

The following structure was confirmed by MS:

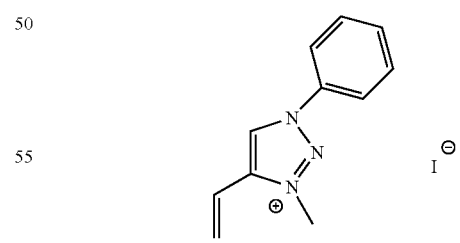

Example 4

Preparation of 1-benzyl-3-methyl-4-phenyl-1H-1,2,3-triazol-3-ium iodide (4-I)

In a 40 mL vial, (azidomethyl)benzene (8.00 g, 60.1 mmol), phenylacetylene (7.47 ml, 68.0 mmol) (Sigma Aldrich, as received), copper (II) sulfate (0.13 g, 0.814 mmol) and Water (Ratio: 1.000, Volume: 20 ml)/MeOH (Ratio: 5.50, Volume: 110 ml) to give a yellow suspension. Sodium ascorbate (0.21 g, 1.040 mmol) was added to the mixture. The reaction was stirred for 23 hours. Water was added to the reaction and the 1-benzyl-4-phenyl-1H-1,2,3-triazole was recrystallized with 100 mL of acetone. The crystal was filtered and dried in vacuo.

1-benzyl-4-phenyl-1H-1,2,3-triazole (0.52 g, 2.197 mmol) prepared above and iodomethane (2 ml, 32.0 mmol) were added to a 20 mL vial. The reaction was heated at 40° C. for 3 days. The iodomethane was allowed to evaporate in the hood. The crude product was dissolved with 2 mL CH$_2$Cl$_2$ under reflux. The solution was precipitated into a mixture of acetone, ethyl acetate and hexane. The yellow solid was collected and dried in vacuo.

The following structure was confirmed via NMR:

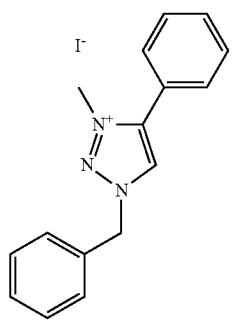 [SMILES: C[n+]1nn(Cc2ccccc2)cc1-c1ccccc1 ; [I-]]

Yield: quantitative. $_1$H NMR (700 MHz, CDCl$_3$): δ 4.23 (s, 3H), 5.92 (s, 2H), 7.28 (s, 3H), 7.35-7.47 (m, 3H), 7.61 (s, 4H) and 9.29 (s, 1H) ppm. $_{13}$C NMR (176 MHz, CDCl$_3$): δ 39.5, 57.0, 121.0, 128.7, 129.0, S8 129.3, 129.3, 129.6, 130.9, 131.6 and 142.6 ppm. Mass Spec: calculated for C$_{16}$H$_{16}$IN$_3$, 377.04. found 376.75.

Preparation of
1-benzyl-3-methyl-4-phenyl-1H-1,2,3-triazol-3-ium
Tf$_2$N

A corresponding triazolium IL with an anion of Tf$_2$N was formed in a typical ion-exchange reaction by refluxing about 1.0 mol of the triazolium iodide prepared above and 1.2 mol of lithium bis[(trifluoromethyl)sulfonyl]amide for more than 12 hours in acetonitrile. The solution was concentrated and dissolved in a mixture of ethyl acetate and water. The organic layer was collected, washed three times with water, dried with MgSO$_4$, filtered, concentrated, dried in vacuo and characterized as follows. The following structure was confirmed:

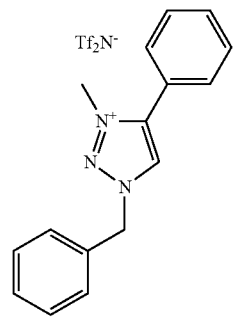 [SMILES: "Tf2N-" ; C[n+]1nn(Cc2ccccc2)cc1-c1ccccc1]

Yield: 84%. $_1$H NMR (400 MHz, CDCl$_3$): δ 4.25 (s, 3H), 5.77 (s, 2H), 7.37-7.71 (m, 10H) and 8.26 (s, 1H) ppm. $_{13}$C NMR (101 MHz, CDCl$_3$): δ 38.6, 57.9, 115.0 (CF$_3$), 143.8. (CF$_3$), 121.4 (CF$_3$), 121.6, 124.6 (CF$_3$), 127.7, 129.3, 129.7, 129.7, 130.3, 130.7, 132.1 and 143.8. $_{19}$F NMR (471 MHz, CDCl$_3$): δ −81.62 ppm. Mass Spec: calculated for C$_{18}$H$_{16}$F$_6$N$_4$O$_4$S$_2$, 530.05. found 529.99.

Example 5

Preparation of 1-benzyl-3-methyl-4-propyl-1H-1,2,
3-triazol-3-ium iodide (4p-I)

In a 40 mL vial, (azidomethyl)benzene, pent-1-yne, copper (II) sulfate and water:MeOH (1:5.5 v/v) were mixed and sodium ascorbate was added to the mixture. The reaction was stirred overnight at room temperature. The reaction was monitored by using TLC using ethyl acetate as the eluent. When the reaction seemed complete, water was added to the reaction and the 1-benzyl-4-propyl-1H-1,2,3-triazole was recrystallized with 100 mL of acetone. The crystal was filtered and dried in vacuo.

1-benzyl-4-propyl-1H-1,2,3-triazole prepared above and excess iodomethane were added to a 20 mL vial. The reaction was heated at 40° C. for 3 days. The iodomethane was allowed to evaporate in the hood. The crude product was dissolved with 2 mL CH$_2$Cl$_2$ under reflux. The solution was precipitated into a mixture of acetone, ethyl acetate and hexane and dried in vacuo. The following structure was confirmed:

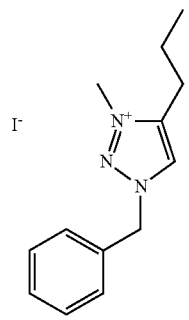 [SMILES: [I-] ; CCCc1cn(Cc2ccccc2)n[n+]1C]

Yield: quantitative. $_1$H NMR (500 MHz, CDCl$_3$): δ 0.93 (t, J=7.3 Hz, 3H), 1.69 (sxt, J=7.6 Hz, 2H), 2.80 (t, J=7.5 Hz, 2H), 4.21 (s, 3H), 5.84 (s, 2H), 7.27-7.29 (m, 3H), 7.50-7.54 (m, 2H) and 9.08 (s, 1H) ppm. $_{13}$C NMR (126 MHz, CDCl$_3$): δ 13.43, 20.26, 25.47, 38.92, 56.83, 128.6, 129.1, 129.3, 129.6, 131.2 and 144.2 ppm. Mass Spec: calculated for C$_{13}$H$_{18}$IN$_3$, 343.05. found 342.99.

Preparation of
1-benzyl-3-methyl-4-propyl-1H-1,2,3-triazol-3-ium
Tf₂N

A corresponding triazolium IL with an anion of Tf₂N was formed in a typical ion-exchange reaction by refluxing about 1.0 mol of the triazolium iodide prepared above and 1.2 mol of lithium bis[(trifluoromethyl)sulfonyl]amide for more than 12 hours in acetonitrile. The solution was concentrated and dissolved in a mixture of ethyl acetate and water. The organic layer was collected, washed three times with water, dried with MgSO₄, filtered, concentrated, dried in vacuo and characterized as follows. The following 1-benzyl-3-methyl-4-propyl-1H-1,2,3-triazol-3-ium Tf₂N structure was confirmed:

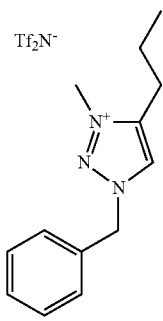 [SMILES: "Tf2N-" ; CCCc1cn(Cc2ccccc2)n[n+]1C]

Yield: quantitative. $_1$H NMR (400 MHz, CDCl₃): δ 1.00 (t, J=7.4 Hz, 3H), 1.71 (sxt, J=7.6 Hz, 2H), 2.73 (t, J=7.5 Hz, 2H), 4.14 (s, 3H), 5.62 (s, 2H), 7.42 (s, 5H), and S12 8.04 (s, 1H) ppm. $_{13}$C NMR (101 MHz, CDCl₃): δ 13.36, 20.26, 25.10, 37.57, 57.58, 115.0 (CF₃), 118.2 (CF₃), 121.4 (CF₃), 124.5 (CF₃), 127.5, 129.4, 129.7, 130.2, 131.0 and 145.1 ppm. $_{19}$F NMR (471 MHz, CDCl₃): δ −81.67 ppm. Mass Spec: calculated for C₁₅H₁₈F₆N₄O₄S₂, 496.07. found 495.97.

Example 6

Preparation of 1-hexyl-3-methyl-4-phenyl-1H-1,2,3-triazol-3-ium iodide (1-I)

1-azidohexane (11.5 g, 90 mmol), ethynylbenzene (9.35 g, 92 mmol) and a 2% solution of copper (II) sulfate (0.12 g, 0.752 mmol) in water were added to a flask with methanol. Sodium ascorbate (0.32 g, 1.615 mmol) was added and the reaction was stirred at room temperature for 23 hours. Additional sodium ascorbate (0.102 g) was added after 12 hours.

The solvent was removed via rotovac. Ethyl acetate (150 mL) and water (50 mL) was added the flask. The organic layer was washed with three times with 50 mL H₂O. The organic layer was dried with Na₂SO₄, filtered and concentrated. The 1-hexyl-4-phenyl-1H-1,2,3-triazole product was dried in vacuo.

1-hexyl-4-phenyl-1H-1,2,3-triazole (0.58 g, 2.53 mmol) and iodomethane (2 ml, 32.0 mmol) were added to a 20 mL vial. The reaction was heated at 40° C. for 3 days. The iodomethane was allowed to evaporate in the hood. The following structure was confirmed:

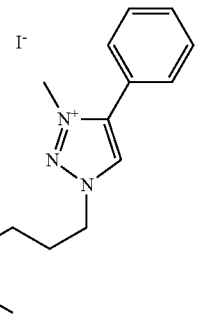

Yield: quantitative. $_1$H NMR (700 MHz, CDCl₃): δ 0.83 (t, 3H), 1.18-1.35 (m, 4H), 1.35-1.45 (m, 2H), 2.05 (quin, J=7.3 Hz, 2H), 4.31 (s, 3H), 4.75 (t, J=6.6 Hz, 2H), 7.50-7.66 (m, 3H), 7.75 (d, J=7.5 Hz, 2H) and 9.48 (s, 1H) ppm. $_{13}$C NMR (176 MHz, CDCl₃,): δ 14.0, 22.4, 25.9, 29.5, 31.0, 39.6, 54.6, 121.8, 129.6, 129.8, 132.0 and 142.9 ppm. Mass Spec: calculated for C₁₅H₂₂IN₃, 371.09. found 370.95.

Preparation of
1-hexyl-3-methyl-4-phenyl-1H-1,2,3-triazol-3-ium
Tf₂N

In a 250 mL round-bottomed flask, lithium bis((trifluoromethyl)sulfonyl)amide (6.67 g, 23.23 mmol) and 1-hexyl-3-methyl-4-phenyl-1H-1,2,3-triazol-3-ium iodide (7.5 g, 20.20 mmol) were mixed in acetonitrile (Volume: 20.20 ml) to give a yellow solution. The solution was refluxed at 120° C. and after about 18 hours the solvent was removed under vacuum. The product was dissolved in 200 ml of DCM and washed with water and brine and dried over MgSO₄, filter and concentrated to yield pale yellow viscous liquid. The IL was left under vacuum overnight. The following structure was confirmed:

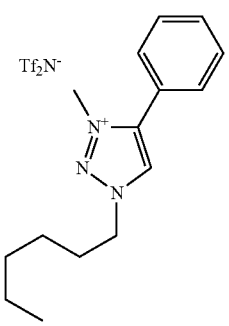 [SMILES: "Tf2N-" ; CCCCCCn1cc(-c2ccccc2)[n+](C)n1]

Yield: 92%. $_1$H NMR (500 MHz, CDCl₃): δ 0.89 (t, J=7.3 Hz, 3H), 1.28-1.37 (m, 4H), 1.37-1.45 (m, 2H), 2.04 (quin, J=7.7 Hz, 2H), 4.23 (s, 3H), 4.57 (t, J=7.9 Hz, 2H), 7.51-7.63 (m, 5H) and 8.40 (s, 1H) ppm. $_{13}$C NMR (126 MHz, CDCl₃): δ 13.94, 22.36, 25.87, 29.11, 30.98, 38.64, 54.46, 116.0 (CF₃), 118.6 (CF₃), 121.2 (CF₃), 121.8, 123.7 (CF₃), 128.1, 129.4, 129.8, 132.1 and 143.6 ppm. $_{19}$F NMR (471 MHz, CDCl₃): δ −81.60 ppm. Mass Spec: calculated for C₁₇H₂₂F₆N₄O₄S₂, 524.10. found 524.07.

Example 7

Preparation of 4-hexyl-3-methyl-1-phenyl-1H-1,2,3-triazol-3-ium iodide (1A-I)

Phenyl azide, oct-1-yne and copper (II) sulfate in t-butanol:water (2:1) mixture were added. Sodium ascorbate was added and the reaction was stirred at room temperature overnight. The solvent was removed under vacuum. The mixture was redesolved in ethyl acetate and water were added to the flask. The organic layer was washed with three times with 50 mL H₂O. The organic layer was dried with Na₂SO₄, filtered and concentrated. The product was further purified using column chromatography using ethylacetate. The 4-hexyl-1-phenyl-1H-1,2,3-triazole product was dried in vacuo.

4-hexyl-1-phenyl-1H-1,2,3-triazole and excess iodomethane were added to a 20 mL vial. The reaction was heated at 40° C. for 3 days. The iodomethane was allowed to evaporate in the hood. The following structure of 4-hexyl-3-methyl-1-phenyl-1H-1,2,3-triazol-3-ium iodide was confirmed:

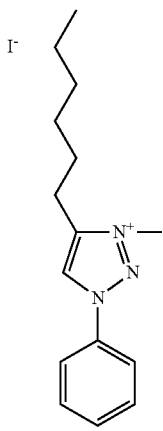 [SMILES: [I-] ; CCCCCCc1cn(-c2ccccc2)n[n+]1C]

Yield: 88%. ¹H NMR (400 MHz, CDCl₃): δ 0.77 (t, J=7.0 Hz, 3H), 1.09-1.45 (m, 6H), 1.80 (quin, J=7.7 Hz, 2H), 2.98 (t, J=7.8 Hz, 2H), 4.38 (s, 3H), 7.41-7.57 (m, 3H), 7.89-8.05 (m, 2H) and 9.47 (s, 1H) ppm. ₁₃C NMR (101 MHz, CDCl₃): δ 13.86, 22.29, 24.05, 27.10, 28.62, 31.03, 39.52, 121.4, 127.2, 130.2, 131.7, 134.5 and 145.9 ppm. Mass Spec: calculated for C₁₅H₂₂IN₃, 371.09. found 370.80.

Preparation of 4-hexyl-3-methyl-1-phenyl-1H-1,2,3-triazol-3-ium Tf₂N

In a 250 mL round-bottomed flask, lithium bis((trifluoromethyl)sulfonyl)amide and 4-hexyl-3-methyl-1-phenyl-1H-1,2,3-triazol-3-ium iodide were mixed in acetonitrile. The solution was refluxed at 120° C. and after about 18 hours the solvent was removed under vacuum. The product was dissolved in 200 ml of DCM and washed with water and brine and dried over MgSO₄, filter and concentrated and left under vacuum overnight. The following structure was confirmed:

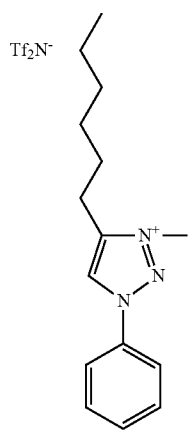 [SMILES: "Tf2N-" ; CCCCCCc1cn(-c2ccccc2)n[n+]1C]

Yield: 95%. ₁H NMR (400 MHz, CDCl₃): δ 0.88 (s, 3H), 1.24-1.37 (m, 4H), 1.37-1.49 (m, 2H), 1.77 (q, J=7.7 Hz, 2H), 2.86 (t, J=7.5 Hz, 2H), 4.26 (s, 3H), 7.54-7.62 (m, 3H), 7.75-7.85 (m, 2H) and 8.49 (s, 1H). ₁₃C NMR (101 MHz, CDCl₃): δ 14.01, 22.49, 23.46, 26.84, 28.78, 31.20, 37.96, 115.1 (CF₃), 118.3 (CF₃), 121.5 (CF₃), 121.6, 124.7 (CF₃), 125.9, 130.5, 132.1, 134.9 and 146.1. ₁₉F NMR (471 MHz, CDCl₃): δ −81.63 ppm. Mass Spec: calculated for C₁₇H₂₂F₆N₄O₄S₂, 524.10. found, 524.25.

Example 8

Preparation of 1-hexyl-3-methyl-4-propyl-1H-1,2,3-triazol-3-ium iodide (1p-I)

1-azidohexane, pent-1-yne and copper (II) sulfate in water were added to a flask with t-butanol. Sodium ascorbate was added and the reaction was stirred at room temperature for 23 hours. Additional sodium ascorbate was added after 12 hours.

The solvent was removed via rotovac. Ethyl acetate (150 mL) and water (50 mL) were added the flask. The organic layer was washed with three times with 50 mL H₂O. The organic layer was dried with Na₂SO₄, filtered and concentrated. The 1-hexyl-4-propyl-1H-1,2,3-triazole product was dried in vacuo. Further purification was carried out using column chromatography using ethylaceate and hexane mixture.

1-hexyl-4-propyl-1H-1,2,3-triazole and excess iodomethane were added to a 20 mL vial. The reaction was heated at 40° C. for 3 days. The iodomethane was allowed to evaporate in the hood. The following structure of 1-hexyl-3-methyl-4-propyl-1H-1,2,3-triazol-3-ium iodide was confirmed:

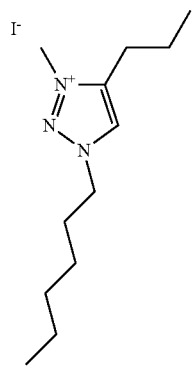

Yield: 95%. ₁H NMR (400 MHz, CDCl₃): δ 0.83 (t, J=7.0 Hz, 3H), 1.04 (t, J=7.4 Hz, 3H), 1.12-1.44 (m, 6H), 1.81 (sxt, J=7.5 Hz, 2H), 1.99 (quin, J=7.5 Hz, 2H), 2.91 (t, J=7.8 Hz, 2H), 4.29 (s, 3H), 4.66 (t, J=7.4 Hz, 2H) and 9.15 (s, 1H) ppm. ₁₃C NMR (101 MHz, CDCl₃): δ 13.77, 13.98, 20.74, S9 22.36, 25.82, 29.51, 30.99, 38.94, 54.30, 129.4 and 144.5 ppm. Mass Spec: calculated for C₁₂H₂₄IN₃, 337.10. found 337.15.

Preparation of
1-hexyl-3-methyl-4-propyl-1H-1,2,3-triazol-3-ium
Tf₂N

In a 250 mL round-bottomed flask, lithium bis((trifluoromethyl)sulfonyl)amide and 1-hexyl-3-methyl-4-propyl-1H-1,2,3-triazol-3-ium iodide were mixed in acetonitrile. The solution was refluxed at 120° C. and after about 18 hours the solvent was removed under vacuum. The product was dissolved in 200 ml of DCM and washed with water and brine and dried over MgSO₄, filtered and concentrated and left under vacuum overnight. The following structure of 1-hexyl-3-methyl-4-propyl-1H-1,2,3-triazol-3-ium Tf₂N was confirmed:

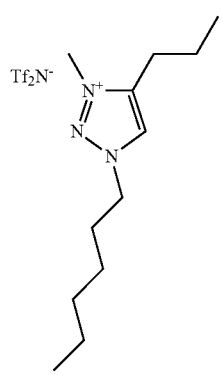

Yield: 59%. $_1$H NMR (500 MHz, CDCl₃): δ 0.87 (t, J=7.5 Hz, 3H), 1.03 (t, J=7.4 Hz, 3H), 1.26-1.38 (m, 6H), 1.75 (sxt, J=7.6 Hz, 2H), 1.95 (quin, J=7.6 Hz, 2H), 2.76 (t, J=8.2 Hz, 2H), 4.15 (s, 3H), 4.47 (t, J=7.6 Hz, 2H) and 8.15 (s, 1H) ppm. $_{13}$C NMR (126 MHz, CDCl₃): δ 13.42, 13.93, 20.34, 22.36, 25.09, 25.82, 29.19, 30.98, 37.51, 54.18, 116.1 S13 (CF₃), 118.6 (CF₃), 121.2 (CF₃), 123.7 (CF₃), 127.9 and 144.9 ppm. $_{19}$F NMR (471 MHz, CDCl₃): δ -81.66 ppm. Mass Spec: calculated for C₁₄H₂₄F₆N₄O₄S₂, 490.11. found 490.06.

Example 9

Preparation of 4-hexyl-3-methyl-1-propyl-1H-1,2,3-triazol-3-ium iodide (1pA-I)

Azidopropane, oct-1-yne and copper (II) sulfate in water were added to a flask with methanol. Sodium ascorbate was added and the reaction was stirred at room temperature for 23 hours. The solvent was removed via rotovac. Ethyl acetate and water were added to the flask. The organic layer was washed with three times with 50 mL H₂O. The organic layer was dried with Na₂SO₄, filtered and concentrated. The 4-hexyl-1-propyl-1H-1,2,3-triazole product was dried in vacuo.

4-hexyl-1-propyl-1H-1,2,3-triazole and excess iodomethane were added to a 20 mL vial. The reaction was heated at 40° C. for 3 days. The iodomethane was allowed to evaporate in the hood. The following structure of 4-hexyl-3-methyl-1-propyl-1H-1,2,3-triazol-3-ium iodide was confirmed:

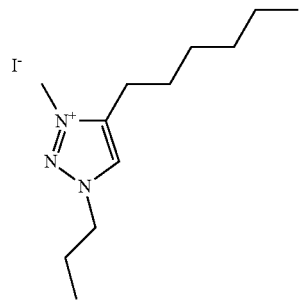

Yield: quantitative. $_1$H NMR (400 MHz, CDCl₃): δ 0.88 (t, J=7.2 Hz, 2H), 1.03 (t, J=7.4 Hz, 3H), 1.27-1.35 (m, 4H). 1.39-1.49 (m, 2H), 1.79 (quin, J=7.6 Hz, 2H), 2.09 (sxt, J=7.3 Hz, 2H), 2.93 (t, J=7.5 Hz, 2H), 4.29 (s, 3H), 4.70 (t, J=7.3 Hz, 2H) and 9.22 (s, 1H) ppm. $_{13}$C NMR (101 MHz, CDCl₃): δ 11.00, 14.16, 22.62, 23.28, 24.21, 27.37, 28.94, 31.38, 38.69, 55.89, 129.7 and 144.8 ppm. Mass Spec: calculated for C₁₂H₂₄IN₃, 337.10. found 336.80.

Preparation of
4-hexyl-3-methyl-1-propyl-1H-1,2,3-triazol-3-ium
Tf₂N

In a 250 mL round-bottomed flask, lithium bis((trifluoromethyl)sulfonyl)amide and 4-hexyl-3-methyl-1-propyl-1H-1,2,3-triazol-3-ium iodide were mixed in acetonitrile. The solution was refluxed at 120° C. and after about 18 hours the solvent was removed under vacuum. The product was dissolved in 200 ml of DCM and washed with water and brine and dried over MgSO₄, filter and concentrated and left under vacuum overnight. The following structure was confirmed:

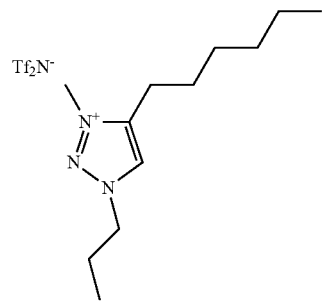

Yield: 67%. 111 NMR (400 MHz, CDCl₃): δ 0.87 (t, J=5.3 Hz, 3H), 0.98 (t, J=7.4 Hz, 3H), 1.21-1.35 (m, 4H), 1.35-1.48 (m, 2H), 1.70 (quin, J=7.4 Hz, 2H), 2.00 (sxt, J=7.2 Hz, 2H), 2.77 (t, J=7.5 Hz, 2H), 4.15 (s, 3H), 4.44 (t, J=7.3 Hz, 2H) and 8.13 (s, 1H) ppm. $_{13}$C NMR (101 MHz, CDCl₃): δ 10.59, 13.96, 22.44, 22.76, 23.34, 26.82, 28.70, 31.19, 37.50, 55.62, 115.1 (CF₃), 118.3 (CF₃), 121.5 (CF₃), 124.7 (CF₃), 127.9 and 145.1 ppm. $_{19}$F NMR (471 MHz, CDCl₃): δ -81.65 ppm. Mass Spec: calculated for C₁₄H₂₄F₆N₄O₄S₂, 490.11. found 489.95.

Example 10

Preparation of 1-{2-[2-(2-methoxyethoxy)ethoxy]ethyl}-3-methyl-4-phenyl-1H-1,2,3-triazol-3-ium iodide (3-I)

Sodium azide (5.37 g, 83 mmol) and 2-(2-(2-methoxyethoxy)ethoxy)ethyl methanesulfonate (20 g, 83 mmol) were added without solvent, the temperature was raised to 60° C. and the mixture stirred for 48 hours. The salts were filtered and ethyl acetate added to precipitate the dissolved salts and filtered again, producing 1-azido-2-(2-(2-methoxyethoxy) ethoxy)ethane.

1-azido-2-(2-(2-methoxyethoxy)ethoxy)ethane (15.0 g, 79 mmol) was mixed with phenylacetylene (8.10 g, 79 mmol) in a 1:3 solution of water:butanol. The mixture was rotovap and the product extracted in ethanolamine and washed multiple times with water and brine, producing 1-(2-(2-(2-methoxyethoxy)ethoxy)ethyl)-4-phenyl-1H-1,2,3-triazole.

The 1-(2-(2-(2-methoxyethoxy)ethoxy)ethyl)-4-phenyl-1H-1,2,3-triazole was refluxed with excess iodomethane in acetonitrile for more than 12 hours and concentrated after cooling to room temperature. The product was rinsed with organic solvent, recrystallized with ethyl acetate and dried in vacuo. The following 1-(2-(2-(2-methoxyethoxy)ethoxy)ethyl)-3-methyl-4-phenyl-1H-1,2,3-triazol-3-ium iodide structure was confirmed:

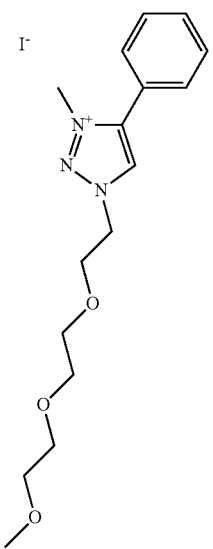 [SMILES: COCCOCCOCCn1cc(-c2ccccc2)[n+](C)n1 ; [I-]]

Yield: 58%. $_1$H NMR (400 MHz, CDCl$_3$): δ 3.21 (s, 3H), 3.37-3.45 (m, 2H), 3.50-m, 4H), 3.70-3.78 (m, 2H), 4.13 (t,=4.9 Hz, 2H), 4.31 (s, 3H), 4.97 (t, J=4.8 Hz, 2H), −7.64 (m, 3H), 7.74 (dd, J$_1$=7.7 Hz, J$_2$=1.9 Hz, 2H) and 9.12 (s, 1H) ppm. $_{13}$C NMR (101 MHz, CDCl$_3$): δ 39.3, 54.4, 58.9, 67.7, 70.2, 70.3, 70.4, 71.7, 122.0, 129.7, 129.9, 130.0, 131.9 and 143.1 ppm. Mass Spec: calculated for C$_{16}$H$_{24}$IN$_3$O$_3$, 433.09. found 432.70.

Preparation of 1-{2-[2-(2-methoxyethoxy)ethoxy]ethyl}-3-methyl-4-phenyl-1H-1,2,3-triazol-3-ium Tf$_2$N 1-(2-(2-(2-methoxyethoxy)ethoxy)ethyl)-3-methyl-4-phenyl-1H-1,2,3-triazol-3-ium iodide and lithium bis((trifluoromethyl)sulfonyl)amide were mixed in acetonitrile and stirred overnight. The acetonitrile was removed under vacuum and water and DCM added. The organic layer was washed three times with water and brine and dried in vacuum at 110° C. for 48 hours, yielding 1-(2-(2-(2-methoxyethoxy)ethoxy)ethyl)-3-methyl-4-phenyl-1H-1,2,3-triazol-3-ium bis((trifluoromethyl)sulfonyl)amide. The following structure was confirmed:

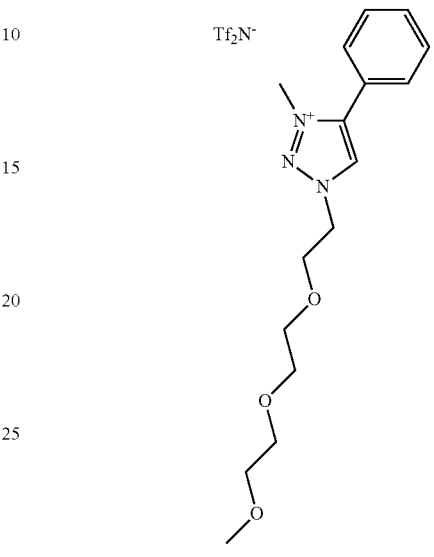

Yield: quantitative. $_1$H NMR (400 MHz, CDCl$_3$): δ 3.18 (s, 3H), 3.37-3.45 (m, 2H), 3.54-3.67 (m, 4H), 3.67-3.74 (m, 2H), 3.98-4.07 (m, 2H), 4.23 (s, 3H), 4.79 (t, J=4.8 Hz, 2H), 7.56-7.66 (m, 5H) and 8.60 (s, 1H) ppm. $_{13}$C NMR (101 MHz, CDCl$_3$): δ 38.4, 54.0, 58.6, 67.4, 70.1, 70.2, 71.6, 116.0 (CF$_3$), 118.5 (CF$_3$), 121.1 (CF$_3$), 121.9, 123.6 (CF$_3$), 129.0, 129.4, 129.7, 132.0 and 143.4 ppm. $_{19}$F NMR (471 MHz, CDCl$_3$): δ −81.54 ppm. Mass Spec: calculated for C$_{18}$H$_{24}$F$_6$N$_4$O$_7$S$_2$, 586.10. found 586.04.

Example 11

Preparation of 1-{2-[2-(2-methoxyethoxy)ethoxy]ethyl}-3-methyl-4-propyl-1H-1,2,3-triazol-3-ium iodide (3p-I)

1-azido-2-(2-(2-methoxyethoxy)ethoxy)ethane (7.0 g, 37.0 mmol), pent-1-yne (2.52 g, 37.0 mmol), sodium (R)-2-((S)-1,2-dihydroxyethyl)-4-hydroxy-5-oxo-2,5-dihydrofuran-3-olate (0.037 g, 0.185 mmol) and copper (II) sulfate (5.90 mg, 0.037 mmol) were added in a mixture of 1:2 (v/v) solution of water:butanol, yielding a product of 1-((3-(2-methoxyethoxy)propoxy)methyl)-4-propyl-1H-1,2,3-triazole.

The 1-((3-(2-methoxyethoxy)propoxy)methyl)-4-propyl-1H-1,2,3-triazole was refluxed with excess iodomethane in acetonitrile for more than 12 hours and concentrated after cooling to room temperature. The product was rinsed with organic solvent, recrystallized with ethyl acetate and dried in vacuo. The following 1-((3-(2-methoxyethoxy)propoxy)methyl)-3-methyl-4-propyl-1H-1,2,3-triazol-3-ium iodide structure was confirmed:

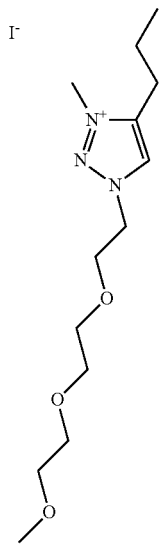 [SMILES: [I-] ; CCCc1cn(CCOCCOCCOC)n[n+]1C]

Yield: quantitative. $_1$H NMR (400 MHz, CDCl$_3$): δ 1.07 (t, J=7.4 Hz, 3H), 1.82 (sxt, J=7.5 Hz, 2H), 3.34 (s, 3H), 3.48-3.53 (m, 2H), 3.59 (m, 4H), 3.67-3.72 (m, 2H), 4.04 (t, J=5.00 Hz, 2H), 4.30 (s, 3H), 4.86 (t, J=4.8 Hz, 2H) and 8.86 (s, 1H) ppm. Mass Spec: calculated for C$_{13}$H$_{26}$IN$_3$O$_3$, 399.10. found 398.80.

Preparation of 1-{2-[2-(2-methoxyethoxy)ethoxy]ethyl}-3-methyl-4-propyl-1H-1,2,3-triazol-3-ium Tf$_2$N 1-(2-(2-(2-methoxyethoxy)ethoxy)ethyl)-3-methyl-4-propyl-1H-1,2,3-triazol-3-ium iodide and lithium bis((trifluoromethyl)sulfonyl)amide were mixed in acetonitrile and stirred overnight. The acetonitrile was removed under vacuum and water and DCM added. The organic layer was washed three times with water and brine and dried in vacuum at 110° C. for 48 hours, yielding 1-(2-(2-(2-methoxyethoxy)ethoxy)ethyl)-3-methyl-4-propyl-1H-1,2,3-triazol-3-ium bis((trifluoromethyl)sulfonyl)amide.
The following structure was confirmed:

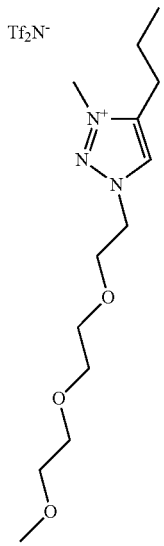 [SMILES: "Tf2N-" ; CCCc1cn(CCOCCOCCOC)n[n+]1C]

Yield: quantitative. $_1$H NMR (500 MHz, CDCl$_3$): δ 1.02 (t, J=7.3 Hz, 3H), 1.73 (sxt, J=7.6 Hz, 2H), 2.75 (t, J=7.9 Hz, 2H), 3.32 (s, 3H), 3.48-3.53 (m, 2H), 3.55-3.60 (m, 4H), 3.61-3.67 (m, 2H), 3.93 (t, J=5.0 Hz, 2H), 4.14 (s, 3H), 4.65 (t, J=4.7 Hz, 2H) and 8.23 (s, 1H) ppm. $_{13}$C NMR (126 MHz, CDCl$_3$): δ 13.38, S14 20.31, 25.01, 37.43, 53.70, 58.89, 67.63, 70.22, 70.32, 71.69, 116.0 (CF$_3$), 118.5 (CF$_3$), 121.1 (CF$_3$), 123.6 (CF$_3$), 128.6 and 144.6 ppm. $_{19}$F NMR (471 MHz, CDCl$_3$): δ −81.61 ppm. Mass Spec: calculated for C$_{15}$H$_{26}$F$_6$N$_4$O$_7$S$_2$, 552.11. found 552.06.

Example 12

Preparation of 3-methyl-4-phenyl-1-(pyridin-4-yl)-1H-1,2,3-triazol-3-ium iodide (5-I)

Approximately equimolar amounts of 4-azidopyridine and phenylacetylene (4.12 ml, 41.8 mmol) were added into a 250 mL round-bottom flask with 50 mL mixture of water/acetone. Copper (II) sulfate and sodium L-ascorbate were added to this solution and the reaction was stirred at room temperature for 24 hours. The solution was filtered and concentrated. Ethyl acetate (200 ml) was added to the concentrated solution. The organic layer was washed twice with 25 mL water, dried with MgSO$_4$, filtered, concentrated and dried in vacuo, producing 4-(4-phenyl-1H-1,2,3-triazol-1-yl)pyridine.
4-(4-phenyl-1H-1,2,3-triazol-1-yl)pyridine, excess methyl iodide, and acetonitrile were added to a 100 mL round-bottom flask and refluxed for about 19 hours. The reaction was concentrated and the resulting solid was recrystallized from ethyl acetate and methanol. The precipitate was filtered and dried in vacuo at 60° C. The following 3-methyl-4-phenyl-1-(pyridin-4-yl)-1H-1,2,3-triazol-3-ium iodide structure was confirmed:

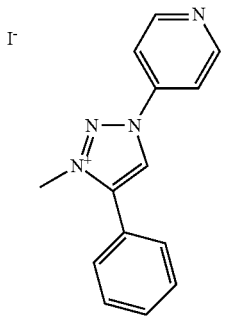 [SMILES: [I-] ; C[n+]1nn(-c2ccncc2)cc1-c1ccccc1]

Yield: quantitative. $_1$H NMR (700 MHz, DMSO-d$_6$): δ 4.38 (s, 3H), 7.46 (t, J=7.5 Hz, 1H), 7.56 (t, J=7.7 Hz, 2H), 7.96 (d, J=7.0 Hz, 2H), 8.70 (d, J=7.5 Hz, 2H), 9.23 (d, J=7.5 Hz, 2H) and S10 9.77 (s, 1H) ppm. $_{13}$C NMR (176 MHz, DMSO-d$_6$): δ 47.55, 116.3, 120.6, 125.6, 128.9, 129.1, 129.3, 146.9, 148.0 and 148.5 ppm. Mass Spec: calculated for C$_{14}$H$_{13}$IN$_4$, 364.02. found 363.80.

Preparation of 3-methyl-4-phenyl-1-(pyridin-4-yl)-1H-1,2,3-triazol-3-ium Tf$_2$N 3-methyl-4-phenyl-1-(pyridin-4-yl)-1H-1,2,3-triazol-3-ium iodide and lithium bis((trifluoromethyl)sulfonyl)amide were mixed in acetonitrile and stirred overnight. The acetonitrile was removed under vacuum and water and DCM added. The organic layer was washed three times with water and brine and dried in vacuum at 110° C. for 48 hours, yielding 3-methyl-4-phenyl-1-(pyridin-4-yl)-1H-1,2,3-triazol-3-ium bis((trifluoromethyl)sulfonyl)amide. The following structure was confirmed:

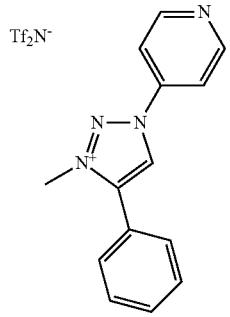 [SMILES: "Tf2N-" ; C[n+]1nn(-c2ccncc2)cc1-c1ccccc1]

Yield: quantitative. $_{19}$F NMR (565 MHz, CDCl$_3$): δ −78.71 ppm. Mass Spec: calculated for C$_{16}$H$_{13}$F$_6$N$_5$O$_4$S$_2$, 517.03. found 516.93.

Example 13

Preparation of 3-methyl-4-propyl-1-(pyridin-4-yl)-1H-1,2,3-triazol-3-ium iodide (5p-I)

4-azidopyridine (4.65 g, 38.7 mmol) and pent-1-yne (4.12 ml, 41:8 mmol) were added into a 250 mL round-bottom flask with 50 mL mixture of water/acetone. Copper(II) sulfate (0.06 g, 0.376 mmol) and sodium L-ascorbate (0.26 g, 1.292 mmol) were added to this solution and the reaction was stirred at room temperature for 24 hours. Additional sodium ascorbate (0.10 g) was added. The solution was filtered and concentrated. Ethyl acetate (200 ml) was added to the concentrated solution. The organic layer was washed twice with 25 mL water, dried with MgSO$_4$, filtered, concentrated and dried in vacuo, producing 4-(4-propyl-1H-1,2,3-triazol-1-yl)pyridine.

4-(4-propyl-1H-1,2,3-triazol-1-yl)pyridine (3.23 g, 17.15 mmol), methyl iodide (15 ml, 240 mmol), and acetonitrile (Volume: 20 ml) were added to a 100 mL round-bottom flask and refluxed for about 19 hours. The reaction was concentrated. The resulting solid was recrystallized from ethyl acetate (100 mL) and methanol (50 mL). The precipitate was filtered and dried in vacuo at 60° C. The following 3-methyl-4-propyl-1-(pyridin-4-yl)-1H-1,2,3-triazol-3-ium iodide structure was confirmed:

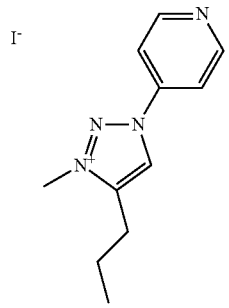

Yield: 67%. $_1$H NMR (400 MHz, DMSO-d$_6$): δ 0.96 (t, J=7.4 Hz, 3H), 1.70 (sxt, J=7.4 Hz, 2H), 2.73 (t, J=7.4 Hz, 2H), 4.37 (s, 3H), 8.65 (d, J=7.5 Hz, 2H), 9.06 (s, 1H) and 9.19 (d, J=7.0 Hz, 2H) ppm. $_{13}$C NMR (101 MHz, DMSO-d$_6$): δ 13.50, 21.65, 26.77, 47.47, 116.0, 121.3, 146.87, 147.8 and 149.6 ppm. Mass Spec: calculated for C$_{11}$H$_{15}$IN$_4$, 330.03. found 330.05.

Preparation of 3-methyl-4-propyl-1-(pyridin-4-yl)-1H-1,2,3-triazol-3-ium Tf$_2$N 3-methyl-4-propyl-1-(pyridin-4-yl)-1H-1,2,3-triazol-3-ium iodide and lithium bis((trifluoromethyl)sulfonyl)amide were mixed in acetonitrile and stirred overnight. The acetonitrile was removed under vacuum and water and DCM added. The organic layer was washed three times with water and brine and dried in vacuum at 110° C. for 48 hours, yielding 3-methyl-4-propyl-1-(pyridin-4-yl)-1H-1,2,3-triazol-3-ium bis((trifluoromethyl)sulfonyl)amide.

The following structure was confirmed:

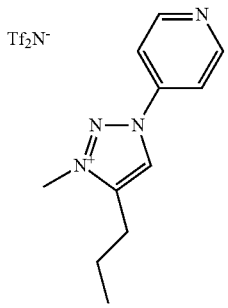

Yield: 30%. $_1$H NMR (400 MHz, DMSO-d$_6$): δ 0.97 (t, J=7.3 Hz, 3H), 1.71 (sxt, J=7.4 Hz, 2H), 2.75 (t, J=7.4 Hz, 2H), 4.35 (s, 3H), 8.64 (d, J=7.0 Hz, 2H), 9.01 (s, 1H) and 9.16 (d, J=6.9 Hz, 2H) ppm. $_{13}$C NMR (101 MHz, DMSO-d$_6$): δ 13.45, 21.71, 26.81, 47.39, 114.7 (CF$_3$), 116.1, 117.9 (CF$_3$), 121.1 (CF$_3$), 121.2, 124.3 (CF$_3$), 147.0, 147.9 and 149.7 ppm. $_{19}$F NMR (565 MHz, CDCl$_3$): δ −78.80 ppm. Mass Spec: calculated for C$_{13}$H$_{15}$F$_6$N$_5$O$_4$S$_2$, 483.05. found 482.99.

Example 14

Preparation of 3-methyl-4-phenyl-1-((trimethylsilyl)methyl)-1H-1,2,3-triazol-3-ium iodide (2-I)

(Chloromethyl)trimethylsilane (1.69 g, 13.80 mmol) and sodium azide (2.42, 37.2 mmol) were added to 5 mL DME. The reaction was stirred for 3 days and dissolved with 15 mL water. Ether was added, and the organic layer was washed thrice with 10 mL water. Ether was removed, and the resulting solution of (azidomethyl)trimethylsilane was used as is.

(Azidomethyl)trimethylsilane (1.6 g, 12.38 mmol), ethynylbenzene (1.30 g, 12.73 mmol), copper(II) sulfate (0.06 g, 0.376 mmol) and sodium (R)-2-((S)-1,2-dihydroxyethyl)-4-hydroxy-5-oxo-2,5-dihydrofuran-3-olate (0.135 g, 0.681 mmol) were added to a 1:2 solution of water:butan-1-ol. The reaction was stirred for 4 days and t-butanol and water were removed, producing a 4-phenyl-1-((trimethylsilyl)methyl)-1H-1,2,3-triazole solid.

4-phenyl-1-((trimethylsilyl)methyl)-1H-1,2,3-triazole (1.0 g, 4.32 mmol) and iodomethane (5 ml, 80 mmol) were added to a vial. The reaction was heated for 19.5 hours. and 5 mL ACN was added. The reaction was heated for another 2 hours. The precipitate was filtered, rinsed with ether and dried in vacuo overnight. The following 3-methyl-4-phenyl-1-((trimethylsilyl)methyl)-1H-1,2,3-triazol-3-ium iodide structure was confirmed:

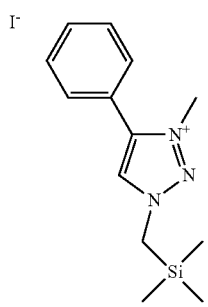 [SMILES: [I-] ; C[n+]1nn(C[Si](C)(C)C)cc1-c1ccccc1]

Yield: quantitative. $_1$H NMR (400 MHz, CDCl$_3$): δ 0.17 (s, 9H), 4.29 (s, 3H), 4.45 (s, 2H), 7.37-7.57 (m, 3H), 7.71 (d, J=7.5 Hz, 2H) and 9.32 (s, 1H) ppm. $_{13}$C NMR (101 MHz, CDCl$_3$): δ –2.40, 39.55, 46.31, 121.7, 129.6, 129.7, 131.8 and 142.7 ppm. Mass Spec: calculated for C$_{13}$H$_{20}$IN$_3$Si, 373.05. found 373.03.

Preparation of 3-methyl-4-phenyl-1-((trimethylsilyl)methyl)-1H-1,2,3-triazol-3-ium Tf$_2$N 4-phenyl-1-((trimethylsilyl)methyl)-1H-1,2,3-triazole (1.02 g, 4.41 mmol) and lithium bis((trifluoromethyl)sulfonyl)amide (1.39 g, 4.83 mmol) were added to a vial with water and heated at 40° C. for 21 hours. The product was dissolved with DCM. The organic layer was washed three times with 5 mL water, dried with MgSO$_4$, filtered, concentrated and dried in vacuo. The following 3-methyl-4-phenyl-1-((trimethylsilyl)methyl)-1H-1,2,3-triazol-3-ium bis((trifluoromethyl)sulfonyl)amide structure was confirmed:

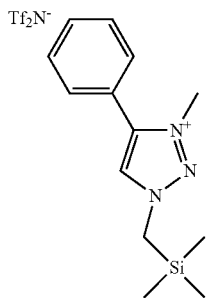 [SMILES: "Tf2N-" ; C[n+]1nn(C[Si](C)(C)C)cc1-c1ccccc1]

Yield: quantitative. $_1$H NMR (400 MHz, CDCl$_3$): δ 0.20 (s, 9H), 4.22 (s, 5H), 7.38-7.71 (m, 5H) and 8.32 (s, 1H) ppm. $_{13}$C NMR (126 MHz, CDCl$_3$): δ –2.84, 38.60, 46.19, 115.2 (CF$_3$), 118.4 (CF$_3$), 121.6 (CF$_3$), 121.8, 124.7 (CF$_3$), 128.2, 129.4, S15 129.9, 132.1 and 143.6 ppm. $_{19}$F NMR (471 MHz, CDCl$_3$): δ –81.61 ppm. Mass Spec: calculated for C$_{15}$H$_{20}$F$_6$N$_4$O$_4$S2Si, 526.06. found 525.96.

Example 15

Preparation of 3-methyl-1-phenyl-4-((trimethylsilyl)methyl)-1H-1,2,3-triazol-3-ium iodide (2B-I)

Trimethylsilylacetylene, phenylazide, copper (II) sulfate and sodium (R)-2-((S)-1,2-dihydroxyethyl)-4-hydroxy-5-oxo-2,5-dihydrofuran-3-olate were added to a 1:2 solution of water:butan-1-ol. The reaction was stirred for 4 days and t-butanol and water were removed, producing a 1-phenyl-4-((trimethylsilyl)methyl)-1H-1,2,3-triazole solid.

1-phenyl-4-((trimethylsilyl)methyl)-1H-1,2,3-triazole and excess iodomethane were added to a vial. The reaction was heated for 19.5 hours. and 5 mL ACN was added. The reaction was heated for another 2 hours. The precipitate was filtered, rinsed with ether and dried in vacuo overnight. The following 3-methyl-1-phenyl-4-((trimethylsilyl)methyl)-1H-1,2,3-triazol-3-ium iodide structure was confirmed:

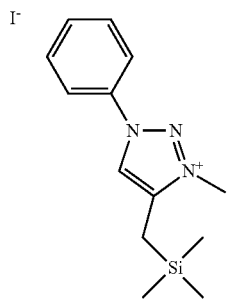 [SMILES: [I-] ; C[n+]1nn(-c2ccccc2)cc1C[Si](C)(C)C]

Yield: 91%. $_1$H NMR (400 MHz, CDCl$_3$): δ 0.15 (m, 9H), 2.66 (s, 2H), 4.32 (s, 3H), 7.44-7.62 (m, 3H), 7.90-8.08 (m, 2H) and 9.52 (s, 1H) ppm. $_{13}$C NMR (101 MHz, CDCl$_3$): δ –1.16, 14.90, 39.19, 121.3, 125.4, 130.3, 131.7, 134.5 and 145.3 ppm. Mass Spec: calculated for C$_{13}$H$_{20}$IN$_3$Si, 373.05. found 372.85.

Preparation of 3-methyl-1-phenyl-4-((trimethylsilyl)methyl)-1H-1,2,3-triazol-3-ium Tf$_2$N 3-methyl-1-phenyl-4-((trimethylsilyl)methyl)-1H-1,2,3-triazol-3-ium iodide and lithium bis((trifluoromethyl)sulfonyl)amide were mixed in acetonitrile and stirred overnight. The acetonitrile was removed under vacuum and water and DCM added. The organic layer was washed three times with water and brine and dried in vacuum at 110° C. for 48 hours, yielding 3-methyl-1-phenyl-4-((trimethylsilyl)methyl)-1H-1,2,3-triazol-3-ium bis((trifluoromethyl)sulfonyl)amide. The following structure was confirmed:

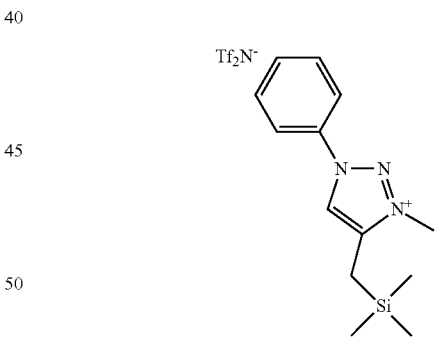

Yield: 77%. $^1$H NMR (400 MHz, CDCl3-d): δ0.16 (s, 9H), 2.44 (s, 2H), 4.22 (s, 3H), 7.61 (m, 3H), 7.84 (m, 2H) and 8.46 (s, 1H). 13C NMR (101 MHz, CDCl$_3$-d): δ–1.73, 14.09, 37.82, 115.0 (CF$_3$), 118.2 (CF$_3$), 121.4 (CF$_3$), 121.6, 124.2, 124.6 (CF3), 126.7, 130.6, 132.2, 134.8 and 145.5. 19F NMR (565 MHz, CDCl$_3$): δ –81.65 ppm. Mass Spec: calculated for C$_{15}$H$_{20}$F$_6$N$_4$O$_4$S$_2$Si, 526.06. found, 526.14.

Example 16

Preparation of 3-methyl-4-propyl-1-((trimethylsilyl)methyl)-1H-1,2,3-triazol-3-ium iodide (2p-I)

(Azidomethyl)trimethylsilane, pent-1-yne, copper (II) sulfate and sodium (R)-2-((S)-1,2-dihydroxyethyl)-4-hydroxy- 5-oxo-2,5-dihydrofuran-3-olate) were added to a 1:2 solution of water:butan-1-ol. The reaction was stirred for about 4 days and t-butanol and water were removed, producing a 4-propyl-1-((trimethylsilyl)methyl)-1H-1,2,3-triazole solid.

4-propyl-1-((trimethylsilyl)methyl)-1H-1,2,3-triazole and excess iodomethane were added to a vial and heated for about 19 and 5 mL ACN was added. The reaction was heated for another 2 hours. The precipitate was filtered, rinsed with ether and dried in vacuo overnight. The following 3-methyl-4-propyl-1-((trimethylsilyl)methyl)-1H-1,2,3-triazol-3-ium iodide structure was confirmed:

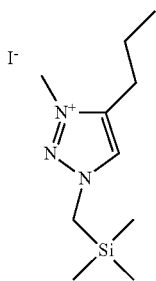

Yield: quantitative. $_1$H NMR (700 MHz, CDCl$_3$): δ 0.19 (s, 9H), 1.05 (t, J=7.5 Hz, 3H), 1.82 (sxt, J=7.6 Hz, 2H), 2.92 (t, J=7.5 Hz, 2H), 4.28 (s, 3H), 4.39 (s, 2H) and 9.07 (s, 1H) ppm. $_{13}$C NMR (176 MHz, CDCl$_3$): δ −2.38, 13.79, 20.87, 25.85, 38.75, 46.24, 129.8 and 144.3 ppm. Mass Spec: calculated for C$_{22}$H$_{10}$IN$_3$Si, 339.06. found 339.50.

Preparation of 3-methyl-4-propyl-1-((trimethylsilyl)methyl)-1H-1,2,3-thiazol-3-ium Tf$_2$N 3-methyl-4-propyl-1-((trimethylsilyl)methyl)-1H-1,2,3-triazol-3-ium iodide and lithium bis((trifluoromethyl)sulfonyl)amide were mixed in acetonitrile and stirred overnight. The acetonitrile was removed under vacuum and water and DCM added. The organic layer was washed three times with water and brine and dried in vacuum at 110° C. for 48 hours, yielding 3-methyl-4-propyl-1-((trimethylsilyl)methyl)-1H-1,2,3-triazol-3-ium bis((trifluoromethyl)sulfonyl)amide.

4-propyl-1-((trimethylsilyl)methyl)-1H-1,2,3-triazole and lithium bis((trifluoromethyl)sulfonyl)amide were added to a vial with water and heated at 40° C. for 21 hours. The product was dissolved with DCM. The organic layer was washed three times with 5 mL water, dried with MgSO$_4$, filtered, concentrated and dried in vacuo. The following 3-methyl-4-propyl-1-((trimethylsilyl)methyl)-1H-1,2,3-triazol-3-ium bis((trifluoromethyl) sulfonyl)amide structure was confirmed:

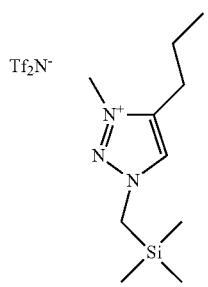

Yield: quantitative. $_1$H NMR (500 MHz, CDCl$_3$): δ 0.14 (s, 9H), 1.01 (t, J=7.4 Hz, 3H), 1.74 (sxt, J=7.6 Hz, 2H), 2.75 (t, J=7.7 Hz, 2H), 4.11 (s, 2H), 4.13 (s, 3H) and 8.05 (s, 1H) ppm. $_{13}$C NMR (126 MHz, CDCl$_3$): δ −2.99, 13.36, 20.35, 24.99, 37.35, 45.87, 76.98, 77.49, 116.1 (CF$_3$), 118.6 (CF$_3$), 121.2 (CF$_3$), 123.7 (CF$_3$), 128.5 and 144.7 ppm. $_{19}$F NMR (471 MHz, CDCl$_3$): δ −81.68 ppm. Mass Spec: calculated for C$_{12}$H$_{22}$F$_6$N$_4$O$_4$S$_2$Si, 492.08. found 492.01.

Example 17

Preparation of 3-methyl-1-propyl-4-((trimethylsilyl)methyl)-1H-1,2,3-triazol-3-ium iodide (2pB-I)

Trimethylsilylacetylene, 1-azidopropane, copper (II) sulfate and sodium (R)-2-((S)-1,2-dihydroxyethyl)-4-hydroxy-5-oxo-2,5-dihydrofuran-3-olate were added to a 1:2 solution of water:butan-1-ol. The reaction was stirred for 4 days and t-butanol and water were removed, producing a 1-propyl-4-((trimethylsilyl)methyl)-1H-1,2,3-triazole solid.

1-propyl-4-((trimethylsilyl)methyl)-1H-1,2,3-triazole and excess iodomethane were added to a vial. The reaction was heated for 19.5 hours and 5 mL ACN was added. The reaction was heated for another 2 hours. The precipitate was filtered, rinsed with ether and dried in vacuo overnight. The following 3-methyl-1-propyl-4-((trimethylsilyl)methyl)-1H-1,2,3-triazol-3-ium iodide structure was confirmed:

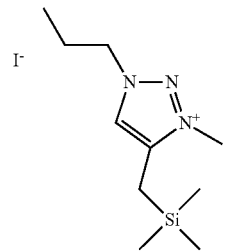

Yield: quantitative. $_1$H NMR (400 MHz, CDCl$_3$): δ 0.21 (s, 9H), 1.04 (t, J=7.4 Hz, 3H), 2.12 (sxt, J=7.4 Hz, 2H), 2.47 (s, 2H), 4.18 (s, 3H), 4.73 (t, J=7.4 Hz, 2H) and 9.23 (s, 1H) ppm. Mass Spec: calculated for C$_{22}$H$_{10}$IN$_3$Si, 339.06. found 339.05.

Preparation of 3-methyl-1-propyl-4-((trimethylsilyl)methyl)-1H-1,2,3-triazol-3-ium Tf$_2$N 3-methyl-1-propyl-4-((trimethylsilyl)methyl)-1H-1,2,3-triazol-3-ium iodide and lithium bis((trifluoromethyl)sulfonyl)amide were mixed in acetonitrile and stirred overnight. The acetonitrile was removed under vacuum and water and DCM added. The organic layer was washed three times with water and brine and dried in vacuum at 110° C. for 48 hours, yielding 3-methyl-1-propyl-4-((trimethylsilyl)methyl)-1H-1,2,3-triazol-3-ium bis((trifluoromethyl)sulfonyl)amide. The following structure was confirmed:

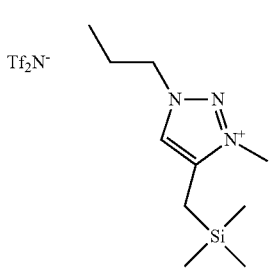

Yield: 45%. $_1$H NMR (400 MHz, CDCl$_3$): δ 0.15 (s, 9H) 1.00 (t, J=7.4 Hz, 3H), 2.03 (sxt, J=7.4 Hz, 2H), 2.35 (s, 2H), 4.13 (s, 3H), 4.49 (t, J=7.3 Hz, 2H) and 8.14 (s, 1H) ppm. $_{19}$F NMR (565 MHz, CDCl$_3$): δ −81.69 ppm. Mass Spec: calculated for C$_{12}$H$_{22}$F$_6$N$_4$O$_4$S$_2$Si 492.08. found 492.07.

Example 18

Prospective Vinyl-Substituted Triazolium ILs

A number of C- and N-vinyl 1,4- and 1,5-substituted 1,2,3-triazoles can be synthesized as described in Nulwala, H., et al., Macromolecules 2010, 43, 5474-5477 [description of synthesis of N-vinyl triazoles] and Takizawa, K., et al., J. Polymer Sci.: Part A: Polymer Chem., vol. 46, 2897-2912 (2008) [description of syntheses of C-vinyl triazoles], which are incorporated by reference herein. It is anticipated that those triazoles can be converted to the corresponding tri-substituted 1,2,3-triazolium ionic liquids having vinyl groups through the addition of an alkyl halide, such a methyl iodide, to the vinyl-containing triazole, which is stirred for approximately two hours. Subsequently, acetonitrile and additional methyl iodide is added and the reaction mixture is stirred, refluxed overnight at 40° C., and distilled in a Rotovac for about 30 minutes.

The resulting tri-substituted, 1,2,3-triazolium halide (iodide) salt may subsequently be subjected to ion exchange in order to replace the anion with a more desired anion. This will be accomplished by adding water and a salt containing the desired anion, such as lithium bis[(trifluoromethyl)sulfonyl] amide, to the triazolium salt and stirring and refluxing the mixture overnight at 80° C. The product can be purified through extraction in organic liquids, distillation of impure compounds and using column chromatography techniques, discarding the aqueous layer and distilling the organic layer.

Example 19

CO$_2$ Solubility of Selected ILs

To characterize CO$_2$ solubility, the gas sorption properties of ionic liquids as a function of time was carried out using a pressure decay sorption system (Setarm PCTPro—2000, Setaram, Inc. Newark, Calif.). All of the ionic liquids were dried in vacuo at room temperature to remove dissolved gases before they were loaded into the pressure decay sorption system. The amount of ionic liquid was between about 0.2 and 0.3 g. CO$_2$ solubility for these ILs was recorded at 37° C. at pressures from 1 to 5 bar. The data were extracted for solubility calculations when the CO$_2$-IL equilibrium reached a plateau (no change in the slope) in the CO$_2$ absorption versus time curve. After 6 hours, this plateau is both visually and mathematically determined to confirm the equilibrium. The general features such as kinetic and equilibrium values in the sorption graph for these ILs are similar. A linear line was fitted for the plot of CO$_2$ molar fraction versus pressure. In FIG. 1, the CO$_2$ molar fraction of triazolium-based ILs was calculated from the resulting equation when the pressure is 3 bar.

Example 20

Thermal Decomposition of Selected ILs

The thermal decomposition temperature ($T_d$) of selected ILs was determined by TGA and evaluated at 5% mass loss of the sample.

Figure 3:
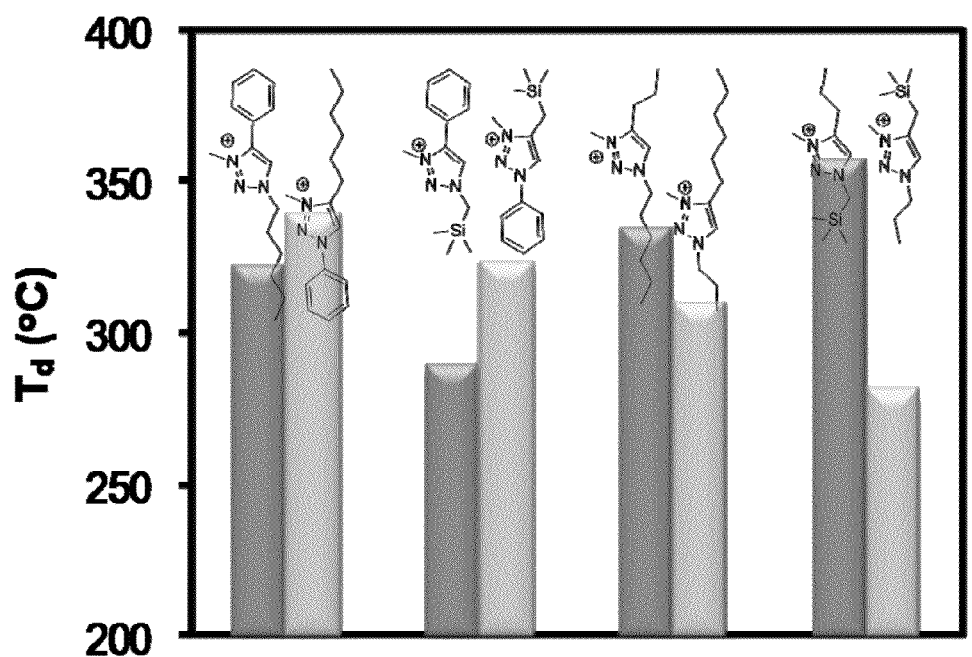
FIG. 3 is a graphical representation of the thermal decomposition temperature of various embodiments with $Tf_2N$ as the anion.

The $T_d$ and other physicochemical properties, including density and melting temperature, of various ILs are presented Table 1. Additional information related to thermal decomposition temperatures of various ionic liquids of the present invention are presented in FIGS. 3 and 4.

TABLE 1

Physicochemical Properties of Various Ionic Liquids

| Ionic Liquid[a] | $V_m$ @ 25° C. (cm$^3$/mol) | Density @ 25° C. (g/cm$^3$) | Density @ 37° C. (g/cm$^3$) | $T_d$ (° C.)[b] | $T_m$ (° C.) |
|---|---|---|---|---|---|
| Ex. 6-Tf$_2$N | 387.06 | 1.3551 | 1.3435 | 323 | |
| Ex. 7-Tf$_2$N | 362.45 | 1.4660 | — | 340 | 71 |
| Ex. 8-Tf$_2$N | 372.77 | 1.3158 | 1.3039 | 335 | |
| Ex. 9-Tf$_2$N | | | | 311 | |
| Ex. 14-Tf$_2$N | | | | 290 | |
| Ex. 15-Tf$_2$N | | | | 324 | |
| Ex. 16-Tf$_2$N | 371.25 | 1.3267 | 1.3148 | 357 | |
| Ex. 17-Tf$_2$N | | | | | |
| Ex. 10-Tf$_2$N | 421.78 | 1.3906 | 1.3709 | 305 | |
| Ex. 11-Tf$_2$N | 398.43 | 1.3867 | 1.3767 | 325 | |
| Ex. 4-Tf$_2$N[c] | 332.37 | 1.5960 | — | 276 | 81 |
| Ex. 5-Tf$_2$N | 341.53 | 1.4536 | 1.4413 | 273 | |
| Ex. 12-Tf$_2$N | | | | 184 | 146 |
| Ex. 13-Tf$_2$N | | | | 190 | |

[a]Numerals correspond to Example numbers
[b]temperature at 5% mass loss of the sample
[c]density measured at 20° C. with error ±0.0007 g/cm$^3$ Example 21

CO$_2$ Selectivity of Selected ILs

The ILs were prepared as described above. A supported ionic liquid membrane (SILM) was made by placing crosslinked nylon supports in a container and depositing the respective ionic liquid on top of the membrane with a pipette. Enough IL was added to completely cover the face of the support and the membrane was allowed to absorb the IL for at least eight hours. The SILMs were then removed from the container and excess IL was removed by blotting.

Testing was performed in a flow system in which the permeate and retentate gas compositions were measured using a gas chromatograph and packed columns. Flows were measured with a digital bubble flow meter. The membrane was placed on the permeate side of a filter holder and a nylon substrate identical to the one used for preparation of the SILM was placed against the SILM on the feed side to reduce mechanical stress. The feed consisted of approximately 30 ml/min of a mixture of CO$_2$ (19.95 mole %), H$_2$ (20.01 mole %) and argon (balance) and a sweep of 6-10 ml/min of argon (99.999%) passed over the permeate side of the membrane. The total pressure was approximately 108 kPa for the feed and the permeate pressure was less than 102 kPa. After introduction of a feed, the system was allowed to reach steady state, and data were recorded for at least 2 hours.

Figure 4:
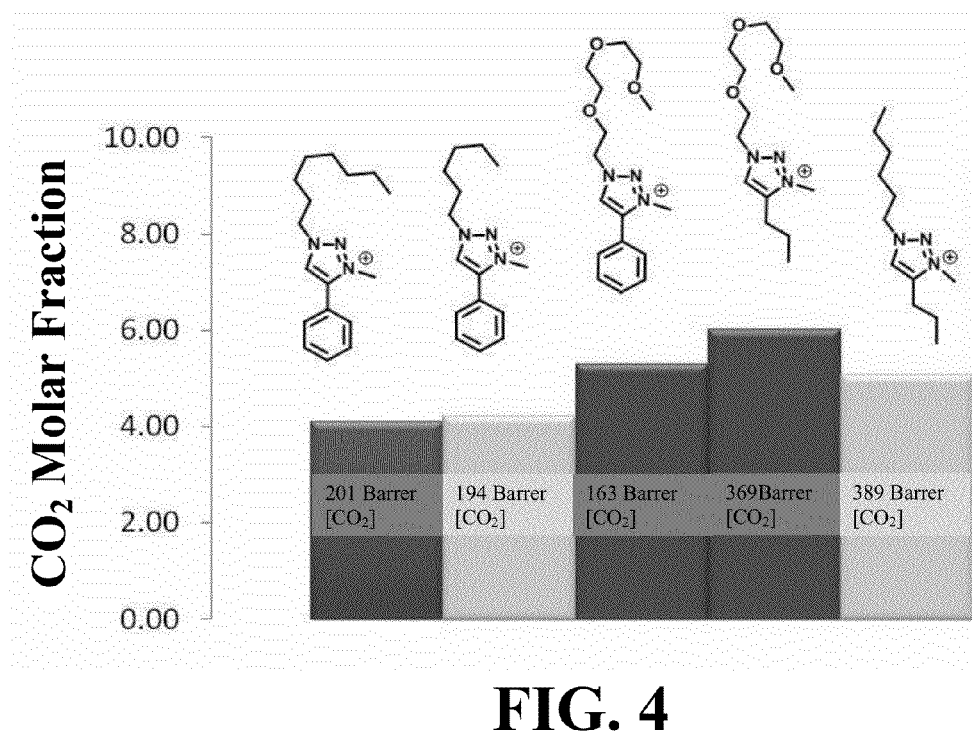
FIG. 4 is a graphical representation of $CO_2/H_2$ selectivity of various embodiments at 37° C.

Measurements of the separation of a mixture ~20 mol % $CO_2$ and ~20 mol % $H_2$ (balance argon) showed selectivities greater than 4 for a supported ionic liquid membrane consisting of the IL depicted in FIG. 4 in a cross-linked Nylon 66 polymeric support.

It is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

It should be noted that ratios, concentrations, amounts, and other numerical data may be expressed herein in a range format or as an approximation. It is to be understood that such a range or approximation is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include .+−.1%, .+−.2%, .+−.3%, .+−.4%, .+−.5%, .+−.6%, .+−.7%, .+−.8%, .+−.9%, or .+−.10%, or more of the numerical value (s) being modified.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a support" includes a plurality of supports. In this specification and in the embodiments that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

We claim:

1. An Ionic Liquid composition comprising:

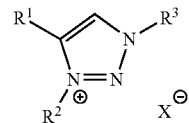

wherein $R^1$ is a vinyl group, $R^3$ is a $C_2$ to $C_{10}$ straight-chain or branched alkane comprising one to three oxygen atoms, and R2 is selected from the group consisting of:
(i) H;
(ii) halogen;
(iii) C1 to C25 straight-chain, branched or cyclic alkane or alkene, optionally substituted with at least one member selected from the group consisting of Cl, Br, F, I, OH, NH2 and SH;

(iv) C1 to C25 straight-chain, branched or cyclic alkane or alkene comprising one to three heteroatoms selected from the group consisting of O, N, Si and S, and optionally substituted with at least one member selected from the group consisting of Cl, Br, F, I, OH, NH2 and SH;
(v) C6 to C20 unsubstituted aryl, or C3 to C25 unsubstituted heteroaryl having one to three heteroatoms independently selected from the group consisting of O, N, Si and S; and,
(vi) C6 to C25 substituted aryl, or C3 to C25 substituted heteroaryl having one to three heteroatoms independently selected from the group consisting of O, N, Si and S; and wherein said substituted aryl or substituted heteroaryl has one to three substituents independently selected from the group consisting of:
(1) C1 to C25 straight-chain, branched or cyclic alkane or alkene, optionally substituted with at least one member selected from the group consisting of Cl, Br, F I, OH, NH2 and SH,
(2) OH,
(3) NH2, and,
(4) SH;
and wherein $X^-$ is an anion.

2. The composition according to claim 1, wherein $R^2$ is a $C_1$ to $C_{25}$ straight-chain or branched alkane.

3. The composition according to claim 2, wherein $X^-$ is selected from the group consisting of iodide, bromide, chloride, acetate and $Tf_2N$.

4. An ionic liquid composition comprising:

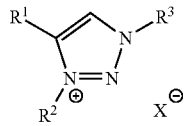

wherein $R^1$ is a vinyl group, $R^2$ is a $C_1$ to $C_5$ alkane and $R^3$ is selected from the group consisting of: (1) $C_2$ to $C_{25}$ straight-chain, branched or cyclic alkane or alkene comprising one to three oxygen atoms, (2) a $C_5$ to $C_{10}$ substituted heteroaryl having one to three nitrogen atoms, and, (3) a $C_6$ to $C_{20}$ unsubstituted aryl group;
and wherein $X^-$ is an anion.

5. An ionic liquid composition selected from the group consisting of: 1-(2-(2-(2-methoxyethoxy)ethoxy)ethyl-3-methyl-4-vinyl-1H-1,2,3-triazol-3-ium bis[(trifluoromethyl)sulfonyl]amide, 1-(2-(2-(2-methoxyethoxy)ethoxy)ethyl-3-methyl-4-vinyl-1H-1,2,3-triazol-3-ium iodide, 3-methyl-1-(pyridine-4-yl)-4-vinyl-1H-1,2,3-triazol-3-ium iodide, 3-methyl-1-(pyridine-4-yl)-4-vinyl-1H-1,2,3-triazol-3-ium bis[(trifluoromethyl)sulfonyl]amide, 3-methyl-1-phenyl-4-vinyl-1H-1,2,3-triazol-3-ium iodide, 3-methyl-1-phenyl-4-vinyl-1H-1,2,3-triazol-3-ium bis[(trifluoromethyl)sulfonyl]amide, 1-benzyl-3-methyl-4-phenyl-1H-1,2,3-triazol-3-ium iodide, 1-benzyl-3-methyl-4-phenyl-1H-1,2,3-triazol-3-ium bis[(trifluoromethyl)sulfonyl]amide, 1-benzyl-3-methyl-4-propyl-1H-1,2,3-triazol-3-ium iodide, 1-benzyl-3-methyl-4-propyl-1H-1,2,3-triazol-3-ium bis[(trifluoromethyl)sulfonyl]amide, 1-hexyl-3-methyl-4-phenyl-1H-1,2,3-triazol-3-ium iodide, 1-hexyl-3-methyl-4-phenyl-1H-1,2,3-triazol-3-ium bis[(trifluoromethyl)sulfonyl]amide, 4-hexyl-3-methyl-1-phenyl-1H-1,2,3-triazol-3-ium iodide, 4-hexyl-3-methyl-1-phenyl-1H-1,2,3-triazol-3-ium bis[(trifluoromethyl)sulfonyl]amide, 1-hexyl-3-methyl-4-propyl-1H-1,2,3-triazol-3-ium iodide, 1-hexyl-3-methyl-4-propyl-1H-1,2,3-triazol-3-ium bis[(trifluoromethyl)sulfonyl]amide, 4-hexyl-3-methyl-1-propyl-1H-1,2,3-triazol-3-ium bis[(trifluoromethyl)sulfonyl]amide, 1-{2-[2-(2-methoxyethoxy)ethoxy]ethyl}-3-methyl-4-phenyl-1H-1,2,3-triazol-3-ium iodide, 1-{2-[2-(2-methoxyethoxy)ethoxy]ethyl}-3-methyl-4-phenyl-1H-1,2,3-triazol-3-ium bis[(trifluoromethyl)sulfonyl]amide, 1-{2-[2-(2-methoxyethoxy)ethoxy]ethyl}-3-methyl-4-propyl-1H-1,2,3-triazol-3-ium iodide, 1-{2-[2-(2-methoxyethoxy)ethoxy]ethyl}-3-methyl-4-propyl-1H-1,2,3-triazol-3-ium bis[(trifluoromethyl)sulfonyl]amide, 3-methyl-4-phenyl-1-(pyridin-4-yl)-1H-1,2,3-triazol-3-ium iodide, 3-methyl-4-phenyl-1-(pyridin-4-yl)-1H-1,2,3-triazol-3-ium bis[(trifluoromethyl)sulfonyl]amide, 3-methyl-4-propyl-1-(pyridin-4-yl)-1H-1,2,3-triazol-3-ium iodide, 3-methyl-4-propyl-1-(pyridin-4-yl)-1H-1,2,3-triazol-3-ium bis[(trifluoromethyl)sulfonyl]amide, 3-methyl-4-phenyl-1-((trimethylsilyl)methyl)-1H-1,2,3-triazol-3-ium iodide, 3-methyl-4-phenyl-1-((trimethylsilyl)methyl)-1H-1,2,3-triazol-3-ium bis[(trifluoromethyl)sulfonyl]amide, 3-methyl-1-phenyl-4-((trimethylsilyl)methyl)-1H-1,2,3-triazol-3-ium iodide, 3-methyl-1-phenyl-4-((trimethylsilyl)methyl)-1H-1,2,3-triazol-3-ium bis[(trifluoromethyl)sulfonyl]amide, 3-methyl-4-propyl-1-((trimethylsilyl)methyl)-1H-1,2,3-triazol-3-ium iodide, 3-methyl-4-propyl-1-((trimethylsilyl)methyl)-1H-1,2,3-triazol-3-ium bis[(trifluoromethyl)sulfonyl]amide, 3-methyl-1-propyl-4-((trimethylsilyl)methyl)-1H-1,2,3-triazol-3-ium iodide, and 3-methyl-1-propyl-4-((trimethylsilyl)methyl)-1H-1,2,3-triazol-3-ium bis[(trifluoromethyl)sulfonyl]amide.

* * * * *